US008632984B2

(12) United States Patent
Uhlen et al.

(10) Patent No.: US 8,632,984 B2
(45) Date of Patent: Jan. 21, 2014

(54) RBM3 AS A MARKER FOR MALIGNANT MELANOMA PROGNOSIS

(75) Inventors: Mathias Uhlen, Stocksund (SE); Fredrik Ponten, Uppsala (SE); Karin Jirstrom, Limhamn (SE)

(73) Assignee: Atlas Antibodies AB, Stockholm (SE)

( * ) Notice: Subject to any disclaimer, the term of this patent is extended or adjusted under 35 U.S.C. 154(b) by 0 days.

(21) Appl. No.: 13/201,742

(22) PCT Filed: Dec. 17, 2009

(86) PCT No.: PCT/EP2009/067419
§ 371 (c)(1),
(2), (4) Date: Dec. 29, 2011

(87) PCT Pub. No.: WO2010/091763
PCT Pub. Date: Aug. 19, 2010

(65) Prior Publication Data
US 2012/0269764 A1    Oct. 25, 2012

Related U.S. Application Data

(60) Provisional application No. 61/169,963, filed on Apr. 16, 2009, provisional application No. 61/233,769, filed on Aug. 13, 2009.

(30) Foreign Application Priority Data

Feb. 16, 2009 (WO) ................ PCT/SE2009/000091
Apr. 16, 2009 (EP) .................................... 09158084
Aug. 13, 2009 (EP) .................................... 09167847

(51) Int. Cl.
G01N 33/53    (2006.01)
C12N 5/07     (2010.01)
A61K 39/395   (2006.01)
A61K 38/00    (2006.01)

(52) U.S. Cl.
USPC ...... 435/7.1; 435/344.1; 424/155.1; 514/19.8

(58) Field of Classification Search
None
See application file for complete search history.

(56) References Cited

U.S. PATENT DOCUMENTS

2009/0252784 A1   10/2009   Houchen et al.

FOREIGN PATENT DOCUMENTS

| WO | WO2006071896 | * | 12/2005 |
| WO | WO 2007/027906 A2 | | 3/2007 |
| WO | WO 2007/084485 A2 | | 7/2007 |
| WO | WO 2009/102261 A1 | | 8/2009 |

OTHER PUBLICATIONS

Danno et al., Decreased expression of mouse Rbm3, a cold-shock protein, in Sertoli cells of cryptorchid testis, Am. J. Pathol., 156, 1685-1692, 2000.*
Baldi, A et al., "Identification of genes down-regulated during melanoma progression: a cDNA array study", Exp. Dermatol., 2003, vol. 12, pp. 213-218.
Danno, S et al., "Decreased expression of mouse Rbm3, a cold-shock protein, in Sertoli cells of cryptorchild testis", Am. J. Pathol., vol. 156, No. 5, May 2000, pp. 1685-1692.
Dresios, J et al., "Cold stress-induced protein Rbm3 binds 60S ribosomal subunits, alters microRNA levels, and enhances global protein synthesis", Proc. Natl. Acad. Sci. USA, vol. 102, No. 6, Feb. 8, 2005, pp. 1865-1870.
European Office Action Corresponding to European Application No. 10 704 928.0; Dated, Dec. 16, 2011; 7 pages.
European Office Action Corresponding to European Application No. 10 704 927.2; Dated, Jan. 9, 2012; 6 pages.
European Office Action Corresponding to European Application No. 09 803 750.0; Dated Feb. 13, 2012; 7 pages.
European Office Action Corresponding to European Application No. 10 705 141.9; Dated Feb. 13, 2012; 7 pages.
International Search Report Corresponding to PCT/EP2009/067419; Date of Mailing: Apr. 7, 2010; 4 pages.
Jogi, A et al., "Nuclear expression of the RNA-binding protein RBM3 is associated with an improved clinical outcome in breast cancer", Modern Pathol., vol. 22, 2009, pp. 1564-1574.
Lleonart, ME., "A new generation of proto-oncogenes: Cold-inducible RNA binding proteins", Biochim. Biophys. Acta, vol. 1805, No. 1, Jan. 1, 2010, pp. 43-52.
Mourtada-Maarabouni, M et al., "The antiapoptotic RBM5/LUCA-15/H37 gene and its role in apoptosis and human cancer: Research update", Scientific World J., vol. 6, pp. 1705-1712, Mar. 15, 2007.
Nilsson, P et al., "Towards a human proteome atlas: High-throughput generation of mono-specific antibodies for tissue profiling", Proteomics, vol. 5, 2005, pp. 4327-4337.
Price, P et al., "The growth rate of metastatic non-seminomatous germ cell testicular tumours measured by marker production doubling time-II. Prognostic significance in patients treated by chemotherapy", Eur. J. Cancer, vol. 26, No. 4, pp. 453-457, 1990.
Richie, JP, "OCT4 staining in testicular tumors. A sensitive and specific marker for seminoma and embryonal carcinoma", J. Urol., 174 (2), 2005, pp. 569-570.

(Continued)

Primary Examiner — Elly-Gerald Stoica
(74) Attorney, Agent, or Firm — Myers Bigel Sibley & Sajovec P.A.

(57) ABSTRACT

A method for determining whether a mammalian subject having a malignant melanoma belongs to a first or a second group, wherein the prognosis of subjects of the first group is better than the prognosis of subjects of the second group is provided. The method comprises the steps of: evaluating an amount of RBM3 protein in at least part of a sample earlier obtained from the subject and determining a sample value corresponding to the evaluated amount; comparing said sample value with a predetermined reference value; and if said sample value is higher than said reference value, concluding that the subject belongs to the first group; and if said sample value is lower than or equal to said reference value, concluding that the subject belongs to the second group.

10 Claims, 12 Drawing Sheets

(56) References Cited

OTHER PUBLICATIONS

Slootstra, JW et al., "Structural aspects of antibody-antigen interaction revealed through small random peptide libraries", *Mol. Diversity*, vol. 1, 1995, pp. 87-96.

Sureban, SM et al., "Translation regulatory factor RBM3 is a proto-oncogene that prevents mitotic catastrophe", Oncogene, Vo. 27, No. 33, Jul. 1, 2008, pp. 4544-4556.

Sutherland, LC et al., "RNA binding motif (RBM) proteins: A novel family of apoptosis modulators?" *J. Cell. Biochem.*, vol. 94, 2005, pp. 5-24.

Wellmann, S et al., "The RNA-binding protein RBM3 Is required for cell proliferation and protects against serum deprivation-induced cell death", *Pediatric Res.*, vol. 67, No. 1, 2010, pp. 35-41.

Zeng, Y et al., "Down-regulating cold shock protein genes impairs cancer cell survival and enhances chemosensitivity", *J. Cell. Biochem.*, vol. 107, No. 1, Mar. 10, 2009, pp. 179-188.

\* cited by examiner

RBM3 AS A MARKER FOR MALIGNANT MELANOMA PROGNOSIS

RELATED APPLICATIONS

This application is a 35 U.S.C. §371 national phase application of PCT Application PCT/EP2009/067419, filed Dec. 17, 2009, which claims priority to PCT/SE2009/000091, filed Feb. 16, 2009. PCT Application PCT/EP2009/067419 also claims priority to U.S. Provisional Application No. 61/169,963, filed Apr. 16, 2009, EP 09158084.5, filed Apr. 16, 2009, U.S. Provisional Application No. 61/233,769, filed Aug. 13, 2009, and EP 09167847.4, filed Aug. 13, 2009. The entire content of each of these applications is incorporated herein by reference.

TECHNICAL FIELD

The present invention relates to the field of malignant melanoma and in particular to prognosis and treatment thereof. Further, it relates to means useful in the establishment of a prognosis or treatment prediction.

BACKGROUND

Cancer

Cancer is one of the most common diseases, and a major cause of death in the western world. In general, incidence rates increase with age for most forms of cancer. As human populations continue to live longer, due to an increase of the general health status, cancer may affect an increasing number of individuals. The cause of most common cancer types is still largely unknown, although there is an increasing body of knowledge providing a link between environmental factors (dietary, tobacco smoke, UV radiation etc) as well as genetic factors (germ line mutations in "cancer genes" such as p53, APC, BRCA1, XP etc) and the risk for development of cancer.

No definition of cancer is entirely satisfactory from a cell biological point of view, despite the fact that cancer is essentially a cellular disease and defined as a transformed cell population with net cell growth and anti-social behavior. Malignant transformation represents the transition to a malignant phenotype based on irreversible genetic alterations. Although this has not been formally proven, malignant transformation is believed to take place in one cell, from which a subsequently developed tumor originates (the "clonality of cancer" dogma). Carcinogenesis is the process by which cancer is generated and is generally accepted to include multiple events that ultimately lead to growth of a malignant tumor. This multi-step process includes several rate-limiting steps, such as addition of mutations and possibly also epigenetic events, leading to formation of cancer following stages of precancerous proliferation. The stepwise changes involve accumulation of errors (mutations) in vital regulatory pathways that determine cell division, asocial behavior and cell death. Each of these changes may provide a selective Darwinian growth advantage compared to surrounding cells, resulting in a net growth of the tumor cell population. A malignant tumor does not only necessarily consist of the transformed tumor cells themselves but also surrounding normal cells which act as a supportive stroma. This recruited cancer stroma consists of connective tissue, blood vessels and various other normal cells, e.g., inflammatory cells, which act in concert to supply the transformed tumor cells with signals necessary for continued tumor growth.

The most common forms of cancer arise in somatic cells and are predominantly of epithelial origin, e.g., prostate, breast, colon, urothelium and skin, followed by cancers originating from the hematopoetic lineage, e.g., leukemia and lymphoma, neuroectoderm, e.g., malignant gliomas, and soft tissue tumors, e.g., sarcomas.

Cancer Diagnostics and Prognostics

Microscopic evaluation of biopsy material from suspected tumors remains the golden standard for cancer diagnostics. To obtain a firm diagnosis, the tumor tissue is fixated in formalin, histo-processed and paraffin embedded. From the resulting paraffin block, tissue sections can be produced and stained using both histochemical, i.e., hematoxylin-eosin staining, and immunohistochemical (IHC) methods. The surgical specimen is then evaluated with pathology techniques, including gross and microscopic analysis. This analysis often forms the basis for assigning a specific diagnosis, i.e., classifying the tumor type and grading the degree of malignancy, of a tumor.

Malignant tumors can be categorized into several stages according to classification schemes specific for each cancer type. The most common classification system for solid tumors is the tumor-node-metastasis (TNM) staging system. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ. Staging of tumors is often based on several forms of examination, including surgical, radiological and histopathological analyses. In addition to staging, for most tumor types there is also a classification system to grade the level of malignancy. The grading systems rely on morphological assessment of a tumor tissue sample and are based on the microscopic features found in a given tumor. These grading systems may be based on the degree of differentiation, proliferation and atypical appearance of the tumor cells. Examples of generally employed grading systems include Gleason grading for prostatic carcinomas and the Nottingham Histological Grade (NHG) grading for breast carcinomas.

Accurate staging and grading is crucial for a correct diagnosis and may provide an instrument to predict a prognosis. The diagnostic and prognostic information for a specific tumor subsequently determines an adequate therapeutic strategy for a given cancer patient. A commonly used method, in addition to histochemical staining of tissue sections, to obtain more information regarding a tumor is immunohistochemical staining. IHC allows for the detection of protein expression patterns in tissues and cells using specific antibodies. The use of IHC in clinical diagnostics allows for the detection of immunoreactivity in different cell populations, in addition to the information regarding tissue architecture and cellular morphology that is assessed from the histochemically stained tumor tissue section. IHC can be involved in supporting the accurate diagnosis, including staging and grading, of a primary tumor as well as in the diagnostics of metastases of unknown origin. The most commonly used antibodies in clinical practice today include antibodies against cell type "specific" proteins, e.g., PSA (prostate), MelanA (melanocytes) and Thyroglobulin (thyroid gland), and antibodies recognizing intermediate filaments (epithelial, mesenchymal, glial), cluster of differentiation (CD) antigens (hematopoetic, sub-classification of lympoid cells) and markers of malignant potential, e.g., Ki67 (proliferation), p53 (commonly mutated tumor suppressor gene) and HER-2 (growth factor receptor).

Aside from IHC, the use of in situ hybridization for detecting gene amplification and gene sequencing for mutation analysis are evolving technologies within cancer diagnostics. In addition, global analysis of transcripts, proteins or metabolites adds relevant information. However, most of these analyses still represent basic research and have yet to be evaluated and standardized for the use in clinical medicine.

Malignant Melanoma

Cutaneous malignant melanoma is a malignant tumor derived from melanocytes located in the skin. Every year, about 160,000 new cases of malignant melanoma are diagnosed world wide. In developed countries, survival rates are high (91% in the USA and 81% in Europe), but developing countries have a considerably lower survival rate of only about 40%. Malignant melanoma is a common skin tumor with a rapidly increasing incidence rate, and since it affects a relatively young patient population each melanoma-related death corresponds to approximately 19 years of life lost. The incidence has increased dramatically in Caucasians in the last few decades, and in the Nordic countries there has been an average increase of approximately 30% every 5 years.

The increased incidence in the last decades is partly explained by altered sun exposure habits of the population, but several hereditary risk factors are also known. Other important risk factors are the number of pigment nevi, the number dysplastic nevi, and skin type. An increased risk is coupled to many nevi, both benign and dysplastic, and fair skin. Familial history of malignant melanomas is a risk factor, and approximately 8-12% of malignant melanoma cases are familial.

Malignant Melanoma Diagnostics

Malignant melanomas are clinically recognized based on the ABCD(E) system, where A stands for assymmetry, B for border irregularity; C for color variation, D for diameter >5 mm, and the proposed E for evolving. Further, an excision biopsy is generally performed in order to make a correct diagnosis by microscopic evaluation.

Infiltrative malignant melanoma is traditionally divided into four principal histopathological subgroups: Superficial spreading melanoma (SSM), nodular malignant melanoma (NMM), lentigo maligna melanoma (LMM), and acral lentiginous melanoma (ALM). Approximately 60% of all melanomas belong to the SSM subtype, 20% to the NMM subtype, and 7% to LMM. ALM arises on palmar and plantar skin along with the nails. This subtype is uncommon in Caucasians, but the most common type found in Orientals and black people. Other rare types also exists, such as desmoplastic malignant melanoma.

A substantial subset of malignant melanomas appear to arise from melanocytic nevi and features of dysplastic nevi are often found in the vicinity of infiltrative melanomas. Melanoma is thought to arise through stages of progression from normal melanocytes or nevus cells through a dysplastic nevus stage and further to an in situ stage before becoming invasive. Some of the subtypes evolve through different phases of tumor progression, which are called radial growth phase (RGP) and vertical growth phase (VGP).

Malignant melanomas are staged according to the American Joint Committee on Cancer (AJCC) TNM-classification system, where Clark level (see below) is considered in T-classification. Stages I and II represent no mestastatic disease and for stage I (T1a/b-2a,N0,M0) prognosis is very good. The 5-year survival for stage I disease is 90-95%, for stage II (T2b-4-b,N0,M0) the corresponding survival rate ranges from 80 to 45%. Stages III (T1a-4-b,N1a-3,M0) and IV (T(aII),N(aII),M1a-c) represent spread disease, and for these stages 5-year survival rates range from 70 to 24%, and from 19 to 7%, respectively. Clark level is the level of tumour invasion into normal skin, and this level has been shown to be a prognostic factor (see below). Clark levels ranges from I to V.

When the primary tumor has a thickness of >1 mm, ulceration, or Clark level IV-V, sentinel node biopsy (SNB) is performed. SNB is performed by identifying the first draining lymph node/s (i.e the SN) from the tumour. This is normally done by injection of radiolabelled colliod particles in the area around the tumour, followed by injection of Vital Blue dye. Close to 100% of all sentinel nodes are detected by this method. Rather than dissection of all regional lymph nodes, which was the earlier standard procedure, only the sentinel nodes are then removed and carefully examined. Following complete lymph node dissection is only performed in confirmed positive cases.

The histopathological features of malignant melanomas vary widely and therefore immunohistochemistry is often used to distinguish malignant melanoma from other tumor forms. Traditionally, S-100 has been used as an immunohistochemical marker of melanocytes, but this protein also stains positive in e.g. Langerhans cells and nerve fibers. Other markers like Melan-A (MART-1), HMB45, and tyrosinase can stain melanocytes more specifically, but since they lack the sensitivity of S100, a combination of S100 with melanocytic markers is often used. In addition to markers of differentiation, proliferation markers may also be used in the differential diagnostics of melanocytic lesions with uncertain malignant potential. The most accepted markers for cells active in the cell cycle are antibodies binding to Ki-67, and frequency of Ki-67 positive melanocytic cells is generally used to distinguish a malignant lesion from benign variants.

Treatment of Malignant Melanoma

Today, the primary treatment of malignant melanoma is radical surgery. Even though survival rates are high after excision of the primary tumour, melanomas tend to metastasize relatively early, and for patients with metastatic melanoma the prognosis is poor, with a 5-year survival rate of less than 10%. Radical removal of distant metastases with surgery can be an option and systemic chemotherapy can be applied, but response rates are normally low (in most cases less than 20%), and most treatment regiments fail to prolong overall survival.

The first FDA-approved chemotherapeutic agent for treatment of metastatic melanoma was dacarbazine (DTIC), which can give response rates of approximately 20%, but where less than 5% may be complete responses. Temozolamid is an analog of DTIC that has the advantage of oral administration, and which have been shown to give a similar response as DTIC. Other chemotherapeutic agents, for example different nitrosureas, cisplatin, carboplatin, and vinca alkaloids, have been used, but without any increase in response rates.

The failure of single chemotherapeutic agents to show effect against metastatic melanomas has led to several clinical trials of multi-drug combinations, but no advantage over treatment with DTIC alone may be stated.

Since chemotherapy is an inefficient treatment method, immunotherapy agents have also been proposed. Most studied are interferon-alpha (IFN-α) and interleukin-2 (IL-2). As single agents they have not been shown to give a better response than conventional treatment, but in combination with chemotherapeutic agents higher response rates have been reported. Radiation treatment may be given as an adjuvant after removal of lymphatic metastases, but malignant melanomas are relatively radioresistant. Radiation treatment might also be used as palliative treatment.

Studies have shown that BRAF mutations are common in both primary and metastatic melanomas, these mutations are reported to be present in 50-70% of all melanomas. This has led to an interest in B-raf inhibitors, such as Sorafenib, as therapeutic agents but routine treatment with such substances are still far ahead.

Prognostics and Treatment Predictive Factors

Patients whom are diagnosed at an advanced stage with metastases generally have a poor prognosis. For patients diagnosed with a localized disease the most important prognostic indicator is the thickness of the tumor measured in mm (Breslow) followed by ulceration. Clark level is important for thin lesions (<1 mm). Other prognostic factors include age, anatomic site of the primary tumor and gender. In Sweden, the 5-year melanoma specific survival rate is 98% for patients in stage IA and 49% for patients in stage IVB. For metastatic melanoma, the number of positive lymph nodes are of importance as well as if the metastases are macro- or microscopic. The sentinel node (SN) status may be a very important prognostic factor, and the 5-year survival of SN-negative patients has been shown to be as high as 90%.

The only serum biomarker included in the AJCC staging system for melanoma, is Lactate dehydrogenase (LDH), which is a marker for disease progression. Patients with distant metastases and elevated LDH levels belong to stage IV M1c. Another serum biomarker of interest is S100B. High S100B levels are associated with disease progression, and a decrease in the S100B level is an indicator of treatment response. Melanoma-inhibiting activity (MIA) is yet another serum biomarker that has been evaluated regarding its prognostic value. Studies have shown that elevated MIA levels are rare in stage I and II disease, whereas in stage III or IV, elevation in MIA levels can be seen in 60-100% of cases.

Some tissue biomarkers that have been identified through tissue microarray studies are RGS1 (associated with reduced relapse-free survival (RFS)), Osteopontin (associated with both reduced RFS and disease-specific survival (DSS), and predictive of SLN metastases), HER3 (associated with reduced survival), and NCOA3 (associated with poor RFS and DSS, and predictive of SLN metastases). However, all these need to be further validated.

Endpoint Analysis

Endpoint analysis for trials with adjuvant treatments for cancer gives important information on how the patients respond to a certain therapy. Overall survival (OS) has long been considered the standard primary endpoint. OS takes into account time to death, irrespective of cause, e.g. if the death is due to cancer or not. Loss to follow-up is censored and regional recurrence, distant metastases, second primary malignant melanomas and second other primary cancers are ignored.

Today, an increasing number of effective treatments available for many types of cancer have resulted in the need for surrogate endpoints to allow for a better evaluation of the effect of adjuvant treatments. Partly due to the long follow-up period required to demonstrate that adjuvant treatments improve OS, this endpoint is often complemented with other clinical endpoints that give an earlier indication on how successful the treatment is.

In the present disclosure, one surrogate endpoint was used, namely disease-free survival (DFS). Analysis of DFS includes time to any event related to the same cancer, i.e. all cancer recurrences and deaths from the same cancer are events.

SUMMARY OF THE PRESENT DISCLOSURE

The inventors have realized that biomarkers are needed to advance malignant melanoma prognostics and treatment prediction.

The following is a non-limiting and itemized listing of embodiments of the present disclosure, presented for the purpose of providing various features and combinations provided by the invention in certain of its aspects.

Items

1. Method for determining whether a mammalian subject having a malignant melanoma belongs to a first or a second group, wherein the prognosis of subjects of the first group is better than the prognosis of subjects of the second group, comprising the steps of:
   a) evaluating an amount of RBM3 protein in at least part of a sample earlier obtained from the subject and determining a sample value corresponding to the evaluated amount;
   b) comparing said sample value with a predetermined reference value; and
      if said sample value is higher than said reference value,
   c1) concluding that the subject belongs to the first group; and
      if said sample value is lower than or equal to said reference value,
   c2) concluding that the subject belongs to the second group.

2. Method for determining a prognosis for a mammalian subject having a malignant melanoma, comprising the steps of:
   a) evaluating an amount of RBM3 protein present in at least part of a sample earlier obtained from the subject and determining a sample value corresponding to the evaluated amount;
   b) comparing the sample value obtained in step a) with a reference value associated with a reference prognosis; and,
      if said sample value is higher than said reference value,
   c1) concluding that the prognosis for said subject is better than said reference prognosis; or
      if said sample value is lower than or equal to said reference value,
   c2) concluding that the prognosis for said subject is worse than or equal to said reference prognosis.

3. Method for determining whether a subject having a malignant melanoma is not in need of a malignant melanoma treatment regimen, comprising the steps of:
   a) evaluating an amount of RBM3 protein present in at least part of a sample earlier obtained from the subject, and determining a sample value corresponding to the evaluated amount;
   b) comparing the sample value obtained in step a) with a reference value; and,
      if said sample value is higher than said reference value,
   c) concluding that said subject is not in need of the malignant melanoma treatment regimen.

4. Non-treatment strategy method for a subject having a malignant melanoma, comprising:
   a) evaluating an amount of RBM3 protein present in at least part of a sample earlier obtained from the subject, and determining a sample value corresponding to the evaluated amount;
   b) comparing the sample value obtained in step a) with a reference value; and,
   if said sample value is higher than said reference value,
   c) refraining from treating said subject with a malignant melanoma treatment regimen.

5. Method for determining whether a mammalian subject having a malignant melanoma belongs to a first or a second group, wherein subjects of the second group is more likely to have a malignant melanoma metastasis than the subjects of the first group, comprising the steps of:
   a) evaluating an amount of RBM3 protein in at least part of a sample earlier obtained from the subject and determining a sample value corresponding to the evaluated amount;
   b) comparing said sample value with a predetermined reference value; and
   if said sample value is higher than said reference value,
   c1) concluding that the subject belongs to the first group; and
   if said sample value is lower than or equal to said reference value,
   c2) concluding that the subject belongs to the second group.

6. Method of examining one or more lymph nodes of a subject having a malignant melanoma, comprising:
   a) evaluating an amount of RBM3 protein present in at least part of a sample from the subject, such as a sample from a primary malignant melanoma tumor, and determining a sample value corresponding to the evaluated amount;
   b) comparing the sample value obtained in step a) with a reference value; and, if said sample value is equal to or lower than said reference value,
   c) performing node biopsy, such as a sentinel node biopsy, on at least one lymph node, wherein the biopsy may be used for establishing whether the malignant melanoma of said subject has spread to the respective lymph node.

7. Method of treatment of a subject having a malignant melanoma, comprising:
   a) evaluating an amount of RBM3 protein present in at least part of a sample from the subject and determining a sample value corresponding to the evaluated amount;
   b) comparing the sample value obtained in step a) with a reference value; and, if said sample value is equal to or lower than said reference value,
   c) treating said subject with a malignant melanoma treatment regimen.

8. Method according to item 1 or 2, wherein said prognosis is a probability of survival, such as overall survival or disease-free survival.

9. Method according to item 8, wherein the probability of survival is a probability of five-year, ten-year or 15-year survival.

10. Method according to any one of items 3, 4 and 7, wherein said malignant melanoma treatment regimen comprises adjuvant and/or neo-adjuvant therapy.

11. Method according to any one of items 3, 4, 7 and 10, wherein said malignant melanoma treatment regimen comprises chemotherapy, immunotherapy and/or radiation treatment.

12. Method according to item 11, wherein said chemotherapy comprises application of dacarbazine or temozolamid.

13. Method according to any one of the preceding items, wherein said malignant melanoma is a superficial spreading melanoma (SSM) or a nodular malignant melanoma (NMM).

14. Method according to any one of the preceding items, wherein said sample is a body fluid sample, stool sample or cytology sample.

15. Method according to item 14, wherein said body fluid sample is selected from the group consisting of blood, plasma, serum, cerebral fluid, urine, seminal fluid and exudate.

16. Method according to any one of the preceding items, wherein said sample comprises cells, such as tumor cells, from said subject.

17. Method according to any one of the preceding items, wherein said sample is a skin tissue sample, such as a malignant melanoma tissue sample.

18. Method according to item 16 or 17, wherein the evaluation of step a) is limited to the nuclei of cells of said sample.

19. Method according to item 18, wherein the evaluation of step a) is limited to the nuclei of tumor cells of said sample.

20. Method according to any one of the preceding items, wherein said subject is a human.

21. Method according to any one of the preceding items, wherein said reference value is a value corresponding to a predetermined amount of RBM3 protein in a reference sample.

22. Method according to any preceding item, wherein the sample value of step a) is determined as being either 1, corresponding to detectable RBM3 protein in the sample, or 0, corresponding to no detectable RBM3 protein in the sample.

23. Method according to any preceding item, wherein the reference value of step b) corresponds to a reference sample having no detectable RBM3 protein.

24. Method according to any preceding item, wherein the reference value of step b) is 0.

25. Method according to any one of the preceding items, wherein said reference value is a nuclear fraction, a nuclear intensity, or a function of a nuclear fraction and a nuclear intensity.

26. Method according to item 25, wherein said reference value is a nuclear fraction of 0-75% RBM3 protein positive cells.

27. Method according to item 25, wherein said reference value is an absent, weak or moderate nuclear intensity.

28. Method according to any one of the preceding items, wherein the amino acid sequence of the RBM3 protein comprises a sequence selected from:
   i) SEQ ID NO:1; and
   ii) a sequence which is at least 85% identical to SEQ ID NO:1.

29. Method according to any one of the preceding items, wherein the amino acid sequence of the RBM3 protein comprises or consists of a sequence selected from:
   i) SEQ ID NO:2; and
   ii) a sequence which is at least 85% identical to SEQ ID NO:2.

30. Method according to any one of the preceding items, wherein step a) comprises:
   aI) applying to said sample a quantifiable affinity ligand capable of selective interaction with the RBM3 protein to be evaluated, said application being performed under conditions that enable binding of the affinity ligand to RBM3 protein present in the sample; and aII) quantifying the affinity ligand bound to said sample to evaluate said amount.

31. Method according to any one of items 1-29, wherein step a) comprises:

a1) applying to said sample a quantifiable affinity ligand capable of selective interaction with the RBM3 protein to be quantified, said application being performed under conditions that enable binding of the affinity ligand to RBM3 protein present in the sample;

a2) removing non-bound affinity ligand; and a3) quantifying affinity ligand remaining in association with the sample to evaluate said amount.

32. Method according to item 30 or 31, wherein the quantifiable affinity ligand is selected from the group consisting of antibodies, fragments thereof and derivatives thereof.

33. Method according to item 32, wherein said quantifiable affinity ligand is obtainable by a process comprising a step of immunizing an animal with a peptide whose amino acid sequence consists of a sequence selected from SEQ ID NO:4 and 5.

34. Method according to item 32, wherein said quantifiable affinity ligand is obtainable by a process comprising a step of immunizing an animal with an RBM3 fragment which consists of 20 amino acids or less, such as 15 amino acids or less, and comprises a sequence selected from SEQ ID NO:6-19.

35. Method according to item 32, wherein said quantifiable affinity ligand is obtainable by a process comprising a step of immunizing an animal with an RBM3 fragment which consists of 20 amino acids or less, such as 15 amino acids or less, and comprises a sequence selected from SEQ ID NO:8, 16 and 17.

36. Method according to item 30 or 31, wherein said quantifiable affinity ligand is an oligonucleotide molecule.

37. Method according to item 30 or 31, wherein the quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

38. Method according to any one of items 30-37, wherein said quantifiable affinity ligand is capable of selective interaction with a peptide whose amino acid sequence consists of a sequence SEQ ID NO:1.

39. Method according to any one of items 30-37, wherein said quantifiable affinity ligand is capable of selective interaction with a peptide consisting of an amino acid sequence selected from SEQ ID NO:4 and 5.

40. Method according to any one of items 30-37, wherein said quantifiable affinity ligand is capable of selective interaction with an RBM3 fragment which consists of 20 amino acids or less, such as 15 amino acids or less, and comprises an amino acid sequence selected from SEQ ID NO:6-19.

41. Method according to any one of items 30-37, wherein said quantifiable affinity ligand is capable of selective interaction with an RBM3 fragment which consists of 20 amino acids or less, such as 15 amino acids or less, and comprises a sequence selected from SEQ ID NO:8, 16 and 17.

42. Method according to any one of items 30-41, wherein said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

43. Method according to any one of items 30-42, wherein said quantifiable affinity ligand is detected using a secondary affinity ligand capable of recognizing said quantifiable affinity ligand.

44. Method according to item 43, wherein said secondary affinity ligand is capable of recognizing said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

45. Kit for carrying out a method according to any one of the preceding items, which comprises a) a quantifiable affinity ligand capable of selective interaction with an RBM3 protein; and b) reagents necessary for quantifying the amount of said quantifiable affinity ligand.

46. Kit according to item 45, in which said quantifiable affinity ligand is selected from the group consisting of antibodies, fragments thereof and derivatives thereof.

47. Kit according to item 46, in which said quantifiable affinity ligand is obtainable by a process comprising a step of immunizing an animal with a protein whose amino acid sequence consists of SEQ ID NO:1.

48. Kit according to item 46, in which said quantifiable affinity ligand is obtainable by a process comprising a step of immunizing an animal with a peptide whose amino acid sequence consists of an amino acid sequence selected from SEQ ID NO:4 and 5.

49. Kit according to item 46, in which said quantifiable affinity ligand is obtainable by a process comprising a step of immunizing an animal with an RBM3 fragment which consists of 20 amino acids or less, such as 15 amino acids or less, and comprises an amino acid sequence selected from SEQ ID NO:6-19.

50. Kit according to item 46, in which said quantifiable affinity ligand is obtainable by a process comprising a step of immunizing an animal with an RBM3 fragment which consists of 20 amino acids or less, such as 15 amino acids or less, and comprises an amino acid sequence selected from SEQ ID NO:8, 16 and 17.

51. Kit according to item 45, in which said quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

52. Kit according to item 45, in which said quantifiable affinity ligand is an oligonucleotide molecule.

53. Kit according to any one of items 45-52, in which said quantifiable affinity ligand is capable of selective interaction with an RBM3 protein comprising, or consisting of, a sequence selected from:

i) SEQ ID NO:1; and ii) a sequence which is at least 85% identical to SEQ ID NO:1.

54. Kit according to any one of items 45-53, in which said quantifiable affinity ligand is capable of selective interaction with an RBM3 protein comprising, or consisting of, a sequence selected from:

i) SEQ ID NO:2; and ii) a sequence which is at least 85% identical to SEQ ID NO:2.

55. Kit according to any one of items 45-53, in which said quantifiable affinity ligand is capable of selective interaction with an RBM3 fragment consisting of an amino acid sequence selected SEQ ID NO:4 and 5.

56. Kit according to any one of items 45-53, in which said quantifiable affinity ligand is capable of selective interaction with an RBM3 fragment which consists of 20 amino acids or less, such as 15 amino acids or less, and comprises an amino acid sequence selected from SEQ ID NO:6-19.

57. Kit according to any one of items 45-53, in which said quantifiable affinity ligand is capable of selective interaction with an RBM3 fragment which consists of 20 amino acids or less, such as 15 amino acids or less, and comprises an amino acid sequence selected from SEQ ID NO:8, 16 and 17.

58. Kit according to any one of items 45-57, in which said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

59. Kit according to any one of items 45-58, in which said reagents necessary for quantifying said amount of said quantifiable affinity ligand comprise a secondary affinity ligand capable of recognizing said quantifiable affinity ligand.

60. Kit according to item 59, in which said secondary affinity ligand comprises a label selected from the group consisting of fluorescent dyes or metals, chromophoric dyes, chemiluminescent compounds and bioluminescent proteins, enzymes, radioisotopes, particles and quantum dots.

61. Kit according to any one of items 45-60, further comprising at least one reference sample for provision of a reference value.

62. Kit according to item 61, in which at least one reference sample is a sample comprising no detectable RBM3 protein.

63. Kit according to item 61 or 62, in which at least one reference sample comprises RBM3 protein.

64. Kit according to any one of items 61-63, in which at least one reference sample comprises an amount of RBM3 protein corresponding to a nuclear fraction of 0-75%.

65. Kit according to any one of items 61-64, in which at least one reference sample comprises an amount of RBM3 protein corresponding to a absent, weak or moderate nuclear intensity.

66. Kit according to any one of items 61-65, in which at least one reference sample comprises an amount of RBM3 protein corresponding to a value being higher than said reference value.

67. Kit according to item 66, in which at least one reference sample comprises an amount of RBM3 protein corresponding to a strong nuclear intensity.

68. Kit according to item 66 or 67, in which at least one reference sample comprises an amount of RBM3 protein corresponding to a nuclear fraction of 75% or higher.

69. Kit according to any one of items 61-68, comprising:
a first reference sample comprising an amount of RBM3 protein corresponding to a value (positive reference value) being higher than a reference value; and
a second reference sample comprising an amount of RBM3 protein corresponding to a value (negative reference value) being lower than or equal to said reference value.

70. Kit according to any one of items 61-69, in which said reference sample comprises a cell line.

71. RBM3 protein fragment which consists of 50 amino acids or less and comprises an amino acid sequence selected from SEQ ID NO:4-19.

72. RBM3 protein fragment according to item 71, which consists of 29 amino acids or less.

73. RBM3 protein fragment according to item 71 or 72, which consists of 20 amino acids or less and comprises an amino acid sequence selected from SEQ ID NO:6-19.

74. RBM3 protein fragment according to item 73, which consists of 20 amino acids or less and comprises an amino acid sequence selected from SEQ ID NO:8, 16 and 17.

75. RBM3 protein fragment according to item 73 or 74, which consists of 15 amino acids or less.

76. Use in vitro of an RBM3 protein as a prognostic marker for malignant melanoma.

77. Use according to item 76, wherein said protein is provided in a sample from a subject having a malignant melanoma.

78. Use according to item 77, wherein said sample is a malignant melanoma sample.

79. Use according any one of items 76-78, wherein the amino acid sequence of the RBM3 protein comprises or consists of a sequence selected from:
i) SEQ ID NO:2; and
ii) a sequence which is at least 85% identical to SEQ ID NO:2.

80. Use in vitro of an RBM3 protein, or an antigenically active fragment thereof, for the selection or purification of a prognostic agent for establishing a prognosis for a mammalian subject having a malignant melanoma.

81. Use of an RBM3 protein, or an antigenically active fragment thereof, for the production of a prognostic agent for establishing a prognosis for a mammalian subject having a malignant melanoma.

82. Use according to item 80 or 81, wherein said prognostic agent is an affinity ligand capable of selective interaction with the RBM3 protein or the antigenically active fragment thereof.

83. Use according any one of items 80-82, wherein the amino acid sequence of the RBM3 protein or antigenically active fragment thereof comprises a sequence selected from:
iii) SEQ ID NO:1; and
iv) a sequence which is at least 85% identical to SEQ ID NO:1.

84. Use of an antigenically active fragment according to any one of items 80-82, wherein the fragment is a fragment according to anyone of items 71-75.

85. Affinity ligand, which is obtainable by a process comprising a step of immunizing an animal with a peptide whose amino acid sequence consists of sequence SEQ ID NO:4 or 5 or a RBM3 protein fragment which consists of 20 amino acids or less, such as 15 amino acids or less, and comprises an amino acid sequence selected from SEQ ID NO:6-19.

86. Affinity ligand, which is obtainable by a process comprising a step of immunizing an animal with a peptide whose amino acid sequence consists of SEQ ID NO:5 or a RBM3 protein fragment which consists of 20 amino acids or less, such as 15 amino acids or less, and comprises a sequence selected from SEQ ID NO:8, 16 and 17.

87. Affinity ligand capable of selective interaction with a peptide whose amino acid sequence consists of SEQ ID NO:5 or an RBM3 fragment which consists of 20 amino acids or less, such as 15 amino acids or less, and comprises an amino acid sequence selected from SEQ ID NO:6-19.

88. Affinity ligand capable of selective interaction with a peptide whose amino acid sequence consists of SEQ ID NO:5 or an RBM3 fragment which consists of 20 amino acids or less, such as 15 amino acids or less, and comprises an amino acid sequence selected from SEQ ID NO:8, 16 and 17.

89. Use in vitro of an affinity ligand capable of selective interaction with an RBM3 protein as a prognostic agent for malignant melanoma.

90. Use according to item 89, wherein the affinity ligand is an affinity ligand according to any one of items 85-88.

BRIEF DESCRIPTION OF THE FIGURES

FIG. 1 shows the results of overall survival (OS) analyses of all patients, diagnosed with malignant melanoma.

FIG. 2 shows the results of disease free survival (DSF) analyses of all patients, diagnosed with malignant melanoma.

FIG. 3 shows the results of survival analyses for all patients based on the NF level of RBM3. RBM3 expression was dichotomized into high and low categories. A dotted line represents a high RBM3 level (NF>1%), and a solid line represents a low RBM3 level (NF=0-1%)

FIG. 4 shows the results of survival analyses for all patients based on the NF level of RBM3. RBM3 expression was dichotomized into high and low categories. A dotted line represents a high RBM3 level (NF>75%), and a solid line represents a low RBM3 level (NF=0-75%)

FIG. 5 shows the results of survival analyses for all patients based on the NI level of RBM3. RBM3 expression was dichotomized into high and low categories. A dotted line represents a high RBM3 level (NI>0), and a solid line represents a low RBM3 level (NI=0).

FIG. 6 shows the results of survival analyses for 107 patients diagnosed with SSM or NMM based on the NF level of RBM3. RBM3 expression was dichotomized into high and low categories. A dotted line represents a high RBM3 level (NF>1%), and a solid line represents a low RBM3 level (NF=0-1%).

FIG. 7 shows the results of survival analyses for 63 patients diagnosed with SSM based on the NF level of RBM3. RBM3 expression was dichotomized into high and low categories. A dotted line represents a high RBM3 level (NF>1%), and a solid line represents a low RBM3 level (NF=0-1%).

FIG. 8 shows the results of survival analyses for 44 patients diagnosed with NMM based on the NF level of RBM3. RBM3 expression was dichotomized into high and low categories. A dotted line represents a high RBM3 level (NF>1%), and a solid line represents a low RBM3 level (NF=0-1%).

FIG. 9 shows the results of survival analyses for all 120 patients based on the NF level of RBM3 using the monoclonal antibody 1B5. RBM3 expression was dichotomized into high and low categories. A dotted line represents a high RBM3 level (NF>75%), and a solid line represents a low RBM3 level (NF=0-75%)

FIG. 10 shows the results of survival analyses for all 120 patients based on the NI level of RBM3 using the monoclonal antibody 1B5. RBM3 expression was dichotomized into high and low categories. A dotted line represents a high RBM3 level (NI>1), and a solid line represents a low RBM3 level (NI≤1).

FIG. 11 shows the proportion of subjects having metastases in groups of RBM3 high and RBM3 low subjects, respectively.

DETAILED DESCRIPTION

Figure 1A:
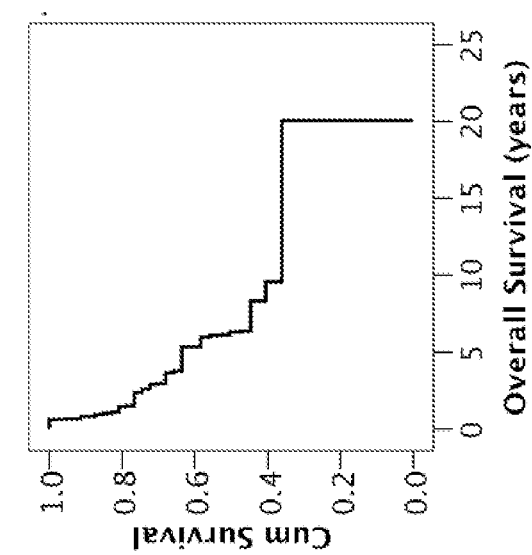
FIG. 1A shows OS for all 119 patients.

As a first aspect of the present disclosure, there is thus provided a method for determining whether a mammalian subject having a malignant melanoma belongs to a first or a second group, wherein the prognosis of subjects of the first group is better than the prognosis of subjects of the second group, comprising the steps of:
 a) evaluating an amount of RBM3 protein in at least part of a sample earlier obtained from the subject and determining a sample value corresponding to the evaluated amount;
 b) comparing said sample value with a predetermined reference value; and
  if said sample value is higher than said reference value,
 c1) concluding that the subject belongs to the first group; and
  if said sample value is lower than or equal to said reference value,
 c2) concluding that the subject belongs to the second group.

The present invention based on an RNA-binding motif 3 (RBM3) protein level as a malignant melanoma status indicator has a number of benefits. As well known by the person skilled in the art, a prognosis may be important for various reasons. Frequently, the prognosis for a malignant melanoma subject reflects the aggressiveness of the cancer. In general, identification of the aggressiveness of a malignant melanoma is of vital importance as it helps a physician selecting an appropriate treatment strategy. For example, if a particularly aggressive form of a cancer is identified, a painful or in any other sense unpleasant treatment which normally is avoided may anyway be considered. Further, if less aggressive forms can be identified, over-treatment may be avoided.

Also, when a primary malignant melanoma tumor has been found, a physician has to decide whether to examine the subject for metastases or not. In addition to the costs involved, such examination may be rather uncomfortable and painful for the subject (the examination normally involves one or more biopsies), and unnecessary examinations should therefore be avoided. On the other hand, not examining a subject that actually has a metastasizing cancer may have fatal consequences. In conclusion, the physician needs to make an informed decision, and an RBM3 protein test may be helpful since the RBM3 protein level is shown herein to correlate with the likelihood of having a metastasis.

In addition, the RBM3 protein, as a marker for which a certain level of expression is correlated with a certain pattern of disease progression, has a great potential for example in a panel for making predictions or prognoses or for the selection of a treatment regimen.

In the method of the first aspect, it is determined whether a malignant melanoma subject belongs to a first or a second group, wherein subjects of the first group generally have a better prognosis than subjects of the second group. The division of malignant melanoma subjects into the two groups is determined by comparing samples values from the subjects with a reference value. In the present disclosure it is shown that various reference values may be employed to discriminate between subjects that generally survived for a comparatively long period (represented by the upper curve) and subjects that generally survived for a comparatively short period (represented by the lower curve). The reference value is thus the determinant for the size of the respective groups; the higher the reference value, the fewer the subjects in the first group and the lower the likelihood that a tested subject belongs to the first group. As the prognosis generally decreases as the sample value decreases, a relatively low reference value may in some instances be selected to identify subjects with a particularly poor prognosis. Guided by the present disclosure, the person skilled in the art may select relevant reference values without undue burden. This is further discussed below.

Figure 6B:
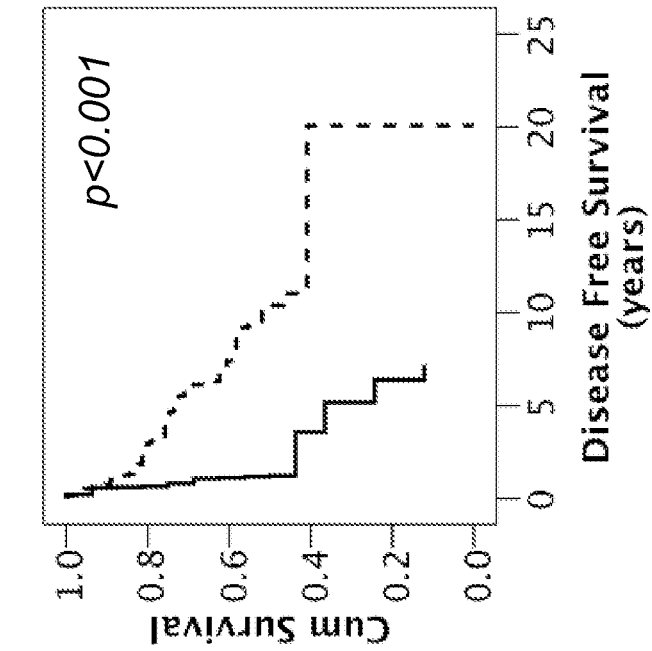
FIG. 6B shows DFS.
Figure 6A:
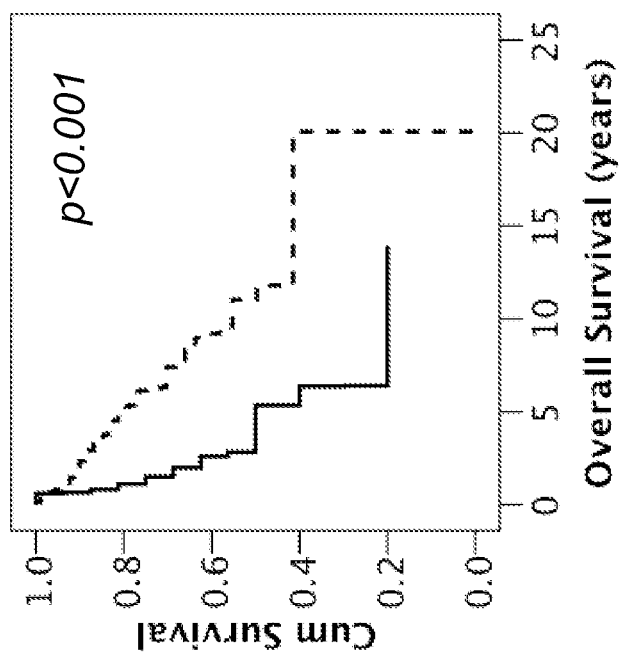
FIG. 6A shows OS.
Figure 7B:
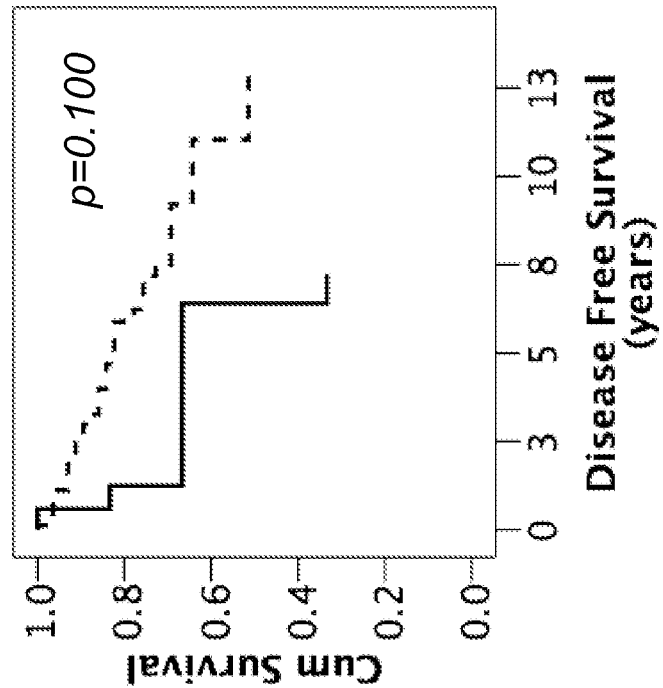
FIG. 7B shows DFS.
Figure 7A:
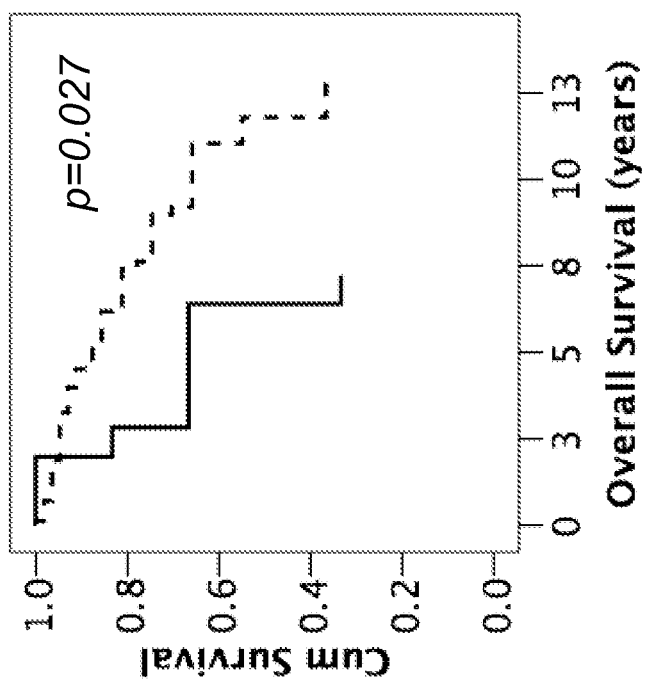
FIG. 7A shows OS.

The first and the second group may consist exclusively of subjects having malignant melanomas of the same or similar stage and/or type (see FIGS. 6-8) as the tested subject. Further, the groups may consist only of subjects having the same or similar age, race, sex, menopausal status, genetic characteristics and/or medical status or history.

Consequently, a physician may use the method according to the first aspect to obtain additional information regarding the prognosis of a malignant melanoma subject, which in turn may help him to make informed decisions regarding following actions.

The prognosis of the tested subject may also be determined relative to a reference prognosis. Accordingly, as a first configuration of the first aspect, there is provided a method for determining a prognosis for a mammalian subject having a malignant melanoma, comprising the steps of:
- a) evaluating an amount of RBM3 protein present in at least part of a sample earlier obtained from the subject and determining a sample value corresponding to the evaluated amount;
- b) comparing the sample value obtained in step a) with a reference value associated with a reference prognosis; and,
    if said sample value is higher than said reference value,
- c1) concluding that the prognosis for said subject is better than said reference prognosis; or
    if said sample value is lower than or equal to said reference value,
- c2) concluding that the prognosis for said subject is worse than or equal to said reference prognosis.

However closely related and covered by the same concept, c1) and c2) provide two alternative conclusions.

Similarly and as a second configuration of the first aspect, there is provided a method for determining whether a prognosis for a mammalian subject having a malignant melanoma is better than a reference prognosis, comprising the steps of:
- a) evaluating an amount of RBM3 protein present in at least part of a sample earlier obtained from the subject and determining a sample value corresponding to the evaluated amount;
- b) comparing the sample value obtained in step a) with a reference value associated with a reference prognosis; and,
    if said sample value is higher than said reference value,
- c) concluding that the prognosis for said subject is better than said reference prognosis.

It follows that as a third configuration of the first aspect, there is provided a method for determining whether a prognosis for a mammalian subject having a malignant melanoma is worse than or equal to a reference prognosis, comprising the steps of:
- a) evaluating an amount of RBM3 protein present in at least part of a sample earlier obtained from the subject and determining a sample value corresponding to the evaluated amount;
- b) comparing the sample value obtained in step a) with a reference value associated with a reference prognosis; and,
    if said sample value is lower than or equal to said reference value,
- c) concluding that the prognosis for said subject is worse than or equal to said reference prognosis.

The inventive concept of the present disclosure may also form the basis for a decision to refrain from a certain treatment regimen.

For example, the prognoses for subjects showing high RBM3 protein levels are generally better than those for subjects showing low RBM3 protein levels, as shown in the attached FIGS. 3-10. Provided with the teachings of the present disclosure, a physician may consider the prognosis of an RBM3 protein high subject as being so favorable that certain adjuvant treatment regimens are avoided and a less aggressive adjuvant treatment regimen is selected instead. For example, mono-therapy may be selected instead of a combination therapy or a therapeutic agent may be given in a lower dose. Also, the decision may be to refrain from any adjuvant treatment if the subject shows a high value.

In conclusion, the present disclosure may relieve subjects from over-treatment.

Thus, as a fourth configuration of the first aspect, there is provided a method for determining whether a subject having a malignant melanoma is not in need of a malignant melanoma treatment regimen, comprising the steps of:
- a) evaluating an amount of RBM3 protein present in at least part of a sample earlier obtained from the subject, and determining a sample value corresponding to the evaluated amount;
- b) comparing the sample value obtained in step a) with a reference value; and,
    if said sample value is higher than said reference value,
- c) concluding that said subject is not in need of the malignant melanoma treatment regimen.

Further, as a fifth configuration of the first aspect, there is provided a non-treatment strategy method for a subject having a malignant melanoma, comprising:
- a) evaluating an amount of RBM3 protein present in at least part of a sample earlier obtained from the subject, and determining a sample value corresponding to the evaluated amount;
- b) comparing the sample value obtained in step a) with a reference value; and,
    if said sample value is higher than said reference value,
- c) refraining from treating said subject with a malignant melanoma treatment regimen.

For example, the refraining of step c) of the fifth configuration may be a refraining from treatment during at least one week from the completion of steps a)-b), such as at least one month from the completion of steps a)-b), such as at least three months from the completion of steps a)-b), such as at least six months from the completion of steps a)-b), such as at least one year from the completion of steps a)-b), such as at least two years from the completion of steps a)-b).

Alternatively, the refraining of step c) may be a refraining from treatment until the next time the method is performed or until recurrence of a malignant melanoma.

As an alternative configuration of the first aspect, there is provided a method for establishing a prognosis for a mammalian subject having a malignant melanoma, comprising the steps of:
- a) evaluating an amount of RBM3 protein present in at least part of a sample from the subject, and determining a sample value corresponding to the evaluated amount; and
- b) correlating the sample value of step a) to the prognosis for the subject.

In the context of the present disclosure, "establishing a prognosis" refers to establishing a specific prognosis or a prognosis interval.

In an embodiment of the alternative configuration, the sample may be an earlier obtained sample.

The correlating of step b) refers to any way of associating survival data to the obtained sample value so as to establish a prognosis for the subject.

In the present disclosure, different RBM3 protein values (sample values) corresponding to various prognoses are presented. Typically, a low sample value is associated with a poorer prognosis than a high sample value. In the method of the third configuration of the first aspect, the sample value is compared to a reference value, and if the sample value is equal to or lower than the reference value, it is concluded that the prognosis for the subject is equal to, or worse than, a reference prognosis associated with the reference value.

Consequently, the method may be adapted to a reference value. In such case, starting from a sample value which under the circumstances is considered to be relevant, a reference value which is equal to the sample value may be selected. Subsequently, a reference prognosis associated with that reference value may be established. Guided by the present disclosure, the person skilled in the art understands how to establish a reference prognosis which corresponds to a given reference value. For example, the relation between sample values and survival data in a relevant group of cancer patients may be examined in line with what is described in Examples, Section 4, below. The procedure described therein may be adapted to a given reference value. Then, a prognosis corresponding to the given reference value may be selected as the reference prognosis.

Also, the method may be adapted to a given reference prognosis. In such case, starting from a reference prognosis which under the circumstances is considered to be relevant, for example for selecting an appropriate therapy, a corresponding reference value may be established. Guided by the present disclosure, the person skilled in the art understands how to establish a reference value which corresponds to a given reference prognosis. For example, the relation between sample values and survival data in a group of cancer patients may be examined as in Examples, Section 4, below, but the procedure described therein may be adapted to establish reference values corresponding to a given reference prognosis. For example, different reference values may be tested until one which correlates with the given reference prognosis is found.

The reasoning above applies mutatis mutandis to the first and second configurations of the first aspect.

Accordingly, the reference prognosis of the first aspect may be based on a previously established prognosis, e.g., obtained by an examination of a relevant population of subjects. Such reference population may be selected to match the tested subject's age, sex, race, malignant melanoma stage, malignant melanoma type and/or medical status and history. Further, a prognosis may be adapted to a background risk in the general population, a statistical prognosis/risk or an assumption based on an examination of the subject. Such examination may also comprise the subject's age, sex, race, malignant melanoma stage, malignant melanoma type and/or medical status and history. Thus, a physician may for example adapt the reference prognosis to the subject's malignant melanoma history, the type and/or stage of the tumor, the morphology of the tumor, the location of the tumor, the presence and spread of metastases and/or further cancer characteristics.

In general, when deciding on a suitable treatment strategy for a patient having malignant melanoma, the physician responsible for the treatment may take several parameters into account, such as the result of an immunohistochemical evaluation, patient age, tumor type, stage and grade, hormone receptor status, general condition and medical history, such as malignant melanoma history. To be guided in the decision, the physician may perform a RBM3 protein test, or order a RBM3 protein test performed, according to the first aspect. Further, the physician may assign to someone else, such as a lab worker, to perform step a), and optionally step b), while performing step c), and optionally b), himself.

Figures 11A, 11B:
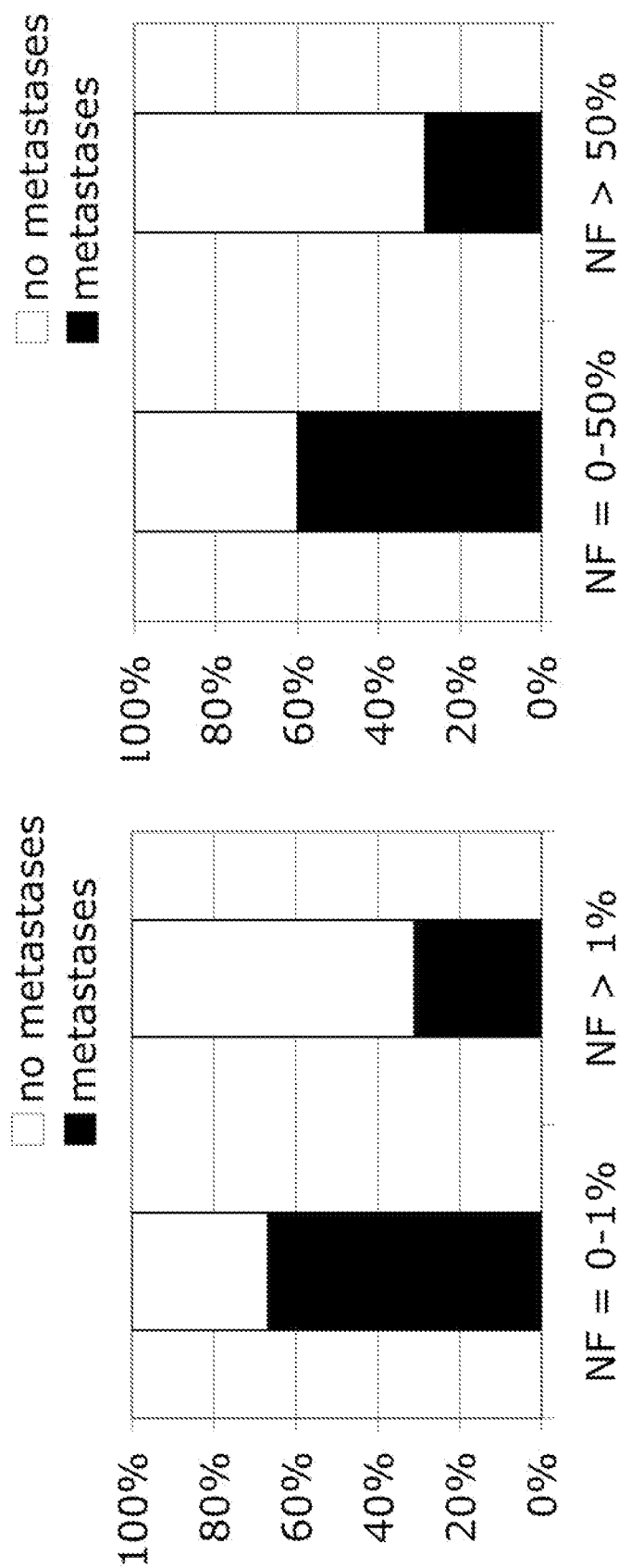
FIG. 11A shows the results obtained using the polyclonal antibody anti-RBM3.
FIG. 11B shows the results obtained using the monoclonal antibody 1B5.

As discussed above, a physician responsible for a malignant melanoma subject should carefully consider whether to examine the subject for metastases of not. Such examination may for example comprise one or more lymph node biopsies, such as sentinel node biopsies. In FIG. 11 it is shown that subjects having RBM3 protein low primary tumors are more likely to have metastases than those having RBM3 protein high primary tumors. The figure indicate that the risk of a metastasis is more than twice as high if the primary tumor is RBM3 protein low than if it is RBM3 protein high.

Thus, as a second aspect of the present disclosure, there is provided a method for determining whether a mammalian subject having a malignant melanoma belongs to a first or a second group, wherein subjects of the second group is more likely to have a malignant melanoma metastasis than the subjects of the first group, comprising the steps of:
- a) evaluating an amount of RBM3 protein in at least part of a sample earlier obtained from the subject and determining a sample value corresponding to the evaluated amount;
- b) comparing said sample value with a predetermined reference value; and
  if said sample value is higher than said reference value,
- c1) concluding that the subject belongs to the first group; and
  if said sample value is lower than or equal to said reference value,
- c2) concluding that the subject belongs to the second group.

As a configuration of the second aspect, there is provided a method of examining one or more lymph nodes of a subject having a malignant melanoma, comprising:
- a) evaluating an amount of RBM3 protein present in at least part of a sample from the subject and determining a sample value corresponding to the evaluated amount;
- b) comparing the sample value obtained in step a) with a reference value; and, if said sample value is equal to or lower than said reference value,
- c) performing node biopsy, such as a sentinel node biopsy, on at least one lymph node.

The biopsy may be used for establishing whether the malignant melanoma of said subject has spread to the respective lymph node.

The inventive concept of the present disclosure may also form the basis for applying various treatment regimes.

For example, the prognosis for subjects showing low RBM3 protein levels is generally worse than those for subjects showing high RBM3 protein levels, as shown in the attached FIGS. 3-10. Provided the teachings of the present disclosure, a physician may thus consider the prognosis of an RBM3 protein low subject as being so poor that a certain adjuvant treatment regimen is appropriate. The present disclosure may thus provide for accurate treatment of a previously undertreated group.

As a third aspect of the present disclosure, there is thus provided a method of treatment of a subject having a malignant melanoma, comprising:
- a) evaluating an amount of RBM3 protein present in at least part of a sample from the subject and determining a sample value corresponding to the evaluated amount;
- b) comparing the sample value obtained in step a) with a reference value; and, if said sample value is equal to or lower than said reference value,
- c) treating said subject with a malignant melanoma treatment regimen.

According to one embodiment, the method may comprise the additional step:
- d) and if said sample value is higher than said reference value, refraining from treating said subject with the malignant melanoma treatment regimen.

In one embodiment of the method of the third aspect, the reference value of step b) may be associated with a reference prognosis and said treatment regimen of step c) may be adapted to a prognosis which is worse than or equal to the reference prognosis. In such an embodiment of the third aspect, the method may comprise the additional step: d) and if said sample value is higher than said reference value, treating said subject with a treatment regimen adapted to a prognosis which is better than the reference prognosis, for which the appropriate treatment regimen may be no treatment.

The physician responsible for the treatment according to the third aspect may assign to someone else, such as a lab worker, to perform step a), and optionally step b), while performing step c), and optionally b), himself.

The method of treatment may be limited to the decision-making and treatment. Thus, as a configuration of the third aspect, there is provided a method of treatment of a subject having a malignant melanoma, comprising:
- α) comparing a sample value corresponding to a level of RBM3 protein in a sample from the subject with a reference value; and,
  if said sample value is equal to or lower than said reference value,
- β) treating said subject with an adjuvant malignant melanoma treatment regimen.

Numerous ways of obtaining a sample value corresponding to a level of RBM3 protein in a sample from a subject are described in the present disclosure.

Regarding step a) of the methods of the present disclosure, an increase in the amount of RBM3 protein typically results in an increase in the sample value, and not the other way around. However, in some embodiments, the evaluated amount may correspond to any of a predetermined number of discrete sample values. In such embodiments, a first amount and a second, increased, amount may correspond to the same sample value. In any case, an increase in the amount of RBM3 protein will not result in a decrease in the sample value in the context of the present disclosure.

However inconvenient, but in an equivalent fashion, the evaluated amounts may be inversely related to sample values if the qualification between step b) and c) is inverted. For example, the qualification between step b) and c) is inverted if the phrase "if the sample value is lower than or equal to the reference value" is replaced with "if the sample value is higher than or equal to the reference value".

In the context of the present disclosure, "prognosis" refers to the prediction of the course or outcome of a disease and its treatment. For example, prognosis may also refer to a determination of chance of survival or recovery from a disease, as well as to a prediction of the expected survival time of a subject. A prognosis may specifically involve establishing the likelihood for survival of a subject during a period of time into the future, such as three years, five years, ten years or any other period of time. A prognosis may further be represented by a single value or a range of values.

Further, in the context of the methods of the present disclosure, "earlier obtained" refers to obtained before the method is performed. Consequently, if a sample earlier obtained from a subject is used in a method, the method does not involve obtaining the sample from the subject, i.e., the sample was previously obtained from the subject in a step separate from the method.

The methods and uses of the present disclosure, except the methods of treatment, may unless otherwise stated be carried out entirely in vitro.

Further, in the context of the present disclosure, "a mammalian subject having a malignant melanoma" refers to a mammalian subject having a primary malignant melanoma tumor or a mammalian subject which has had a primary malignant melanoma tumor removed, wherein the removal of the tumor refers to eradicating the tumor by any appropriate type of surgery or therapy. In the method and use aspects of the present disclosure, "a mammalian subject having a malignant melanoma" also includes the cases wherein the mammalian subject is suspected of having a malignant melanoma at the time of the use or the performance of the method and the malignant melanoma diagnosis is established later.

Further, in the context of the present disclosure, the "reference value" refers to a predetermined value found to be relevant for making decisions or drawing conclusions regarding the prognosis or a suitable treatment strategy for the subject.

Also, in the context of the present disclosure, a reference value being "associated" with a reference prognosis refers to the reference value being assigned a corresponding reference prognosis, based on empirical data and/or clinically relevant assumptions. For example, the reference value may be the average RBM3 protein value in a relevant group of subjects and the reference prognosis may be an average survival in the same group. Further, the reference value does not have to be assigned to a reference prognosis directly derived from prognosis data of a group of subjects exhibiting the reference value. The reference prognosis may for example correspond to the prognosis for subjects exhibiting the reference value or lower. That is, if the reference value is 1 on a scale from 0 to 2, the reference prognosis may be the prognosis of the subjects exhibiting the values 0 or 1. Consequently, the reference prognosis may also be adapted to the nature of the available data. As further discussed above, the reference prognosis may be further adapted to other parameters as well.

Step a) of the methods of the above aspects involve evaluating an amount of RBM3 protein present in at least part of the sample, and determining a sample value corresponding to the amount. The "at least part of the sample" refers to a relevant part or relevant parts of the sample for establishing the prognosis or drawing conclusions regarding suitable treatments. The person skilled in the art understands which part or parts that are relevant under the circumstances present when performing the method. For example, if evaluating a sample comprising cells, the skilled person may only consider the tumor cells, or only the nuclei of tumor cells, of the sample.

Further, in step a) an amount is evaluated and a sample value corresponding to the amount is determined. Consequently, an exact measurement of the amount of RBM3 protein is not required for obtaining the sample value. For example, the amount of RBM3 protein may be evaluated by visual inspection of a prepared and stained tissue sample and the sample value may then be categorized as for example high or low based on the evaluated amount.

The evaluation and determination of step a) requires some kind of processing or manipulation of the sample. It is not possible to determine the sample value by mere inspection. Various techniques, of which some are presented below, for such evaluation and determination, are well known to the skilled person. The methods of the present disclosure are therefore not limited to any specific technique or techniques for the performance of step a).

The treatment regimen of the present disclosure may be an adjuvant and/or a neo-adjuvant therapy. Adjuvant therapy is however preferred since any malignant melanoma is normally surgically removed as soon as possible after detection.

The treatment regimen may for example be chemotherapy, such as application of dacarbazine (DTIC) or temozolamid.

Further, the treatment regimen may for example comprise or consist of immunotherapy, such as application of interferon-alpha (IFN-α) and interleukin-2 (IL-2). The immunotherapy may for example be applied in combination with a chemotherapeutic agent.

The treatment regimen may also comprise radiation therapy.

In case of BRAF mutations, the treatment regimen may involve application of a B-raf inhibitor, such as Sorafenib.

Today, there are not many adjuvant therapies for malignant melanoma available, but the inventors predict that this will change over the coming years and that methods of the present disclosure may be used for determining whether novel treatment regimens shall be applied or not.

Consequently, some of the methods of the present disclosure may yield information which forms the basis of a personalized treatment regimen.

Although the level of RBM3 protein expression is prognostically relevant in a group of patients having any type of malignant melanoma (FIGS. 4, 5, 9 and 10), the prognostic indication is shown herein to be particularly relevant in the group of patients having superficial spreading melanoma (SSM) or nodular malignant melanoma (NMM) (see FIG. 6-8). The correlation between the level of RBM3 protein and prognosis is particularly accentuated in NMM patients (see FIG. 8 compared to FIG. 7).

Accordingly, in embodiments of the first and second aspects, the first and the second group may consist of subjects having cancers of the same stage, grade and/or type as the subject of the method.

Further, in embodiments of the present disclosure, the malignant melanoma may be SSM or NMM.

In embodiments of the present disclosure, the prognosis may be a probability of survival. As explained in the background section, there are several ways to measure "survival". The survival of the present disclosure may for example be overall survival (FIG. 3A, 4A, 5A, 6A, 7A, 8A, 9A or 10A) or disease free survival (FIG. 3B, 4B, 5B, 6B, 7B, 8B, 9B or 10B). Further, the "survival" may be measured over different periods, such as five, ten or 15 years. Accordingly, the survival may be a five-year, ten-year or 15-year survival. Where a reference prognosis is employed, it is of the same type as the prognosis of the subject.

In embodiments of the methods of the above aspects, the sample may be a body fluid sample. For example, the body fluid sample may be selected from the group consisting of blood, plasma, serum, cerebral fluid, urine, lymph, seminal fluid and exudate. Alternatively, the sample may be a cytology sample or a stool sample.

The level of RBM3 protein expression may preferably be measured intracellularly. Thus, the body fluid, cytology or stool sample may for example comprise cells, such as tumor cells.

In further embodiments of the methods of the above aspects, the sample may be a tissue sample, such as an skin tissue sample, such as an malignant melanoma tissue sample, e.g. from a surgical removal of malignant melanoma tissue. The inventors have found that the RBM3 protein level of primary tumors is more prognostically relevant than that of metastases. Consequently, the sample may therefore preferably be derived from the primary tumor.

Further, the inventors have noted that nuclear expression of RBM3 protein is particularly relevant for determining prognoses or selecting treatments (see the figures). Thus, the evaluation of step a) may be limited to the nuclei of cells, such as tumor cells, of said sample. Consequently, when a tissue sample is examined, only the nuclei of tumor cells may be taken into consideration. Such examination may for example be aided by immunohistochemical staining.

The tissue samples in Examples, Section 4, are from male and female humans, and the inventors have found that the prognostic relevance of RBM3 protein is independent of the subject's sex. Accordingly, the subject of the methods of the above aspects may be a human, and further, the subject of the methods of the above aspects may be male or female.

When performing the methods according to the above aspects, it may be convenient to use zero as the reference value, because in such case, it has only to be established in step a) whether RBM3 protein is present in the sample or not. FIGS. 3, 5, 6, 7 and 8 indicate that zero (i.e. no detectable RBM3 protein) is a working cut-off value for establishing two subgroups of significantly different prognoses.

Thus, in embodiments of the methods of the above aspects, the sample value of step a) may be either 1, corresponding to detectable RBM3 protein in the sample, or 0, corresponding to no detectable RBM3 protein in the sample. Consequently, in such embodiments, the evaluation of the sample is digital: RBM3 protein is considered to be either present or not. In the context of the present disclosure, "no detectable RBM3 protein" refers to an amount of RBM3 protein that is so small that it is not, during normal operational circumstances, detectable by a person or an apparatus performing the step a). The "normal operational circumstances" refer to the laboratory methods and techniques a person skilled in the art would find appropriate for performing the methods of the present disclosure.

Accordingly, in embodiments of the methods of the present disclosure, the reference value of step b) may be 0. And it follows that, in further embodiments of the methods of the present disclosure, the reference value of step b) may correspond to a reference sample having no detectable RBM3 protein (see below).

A sample value of RBM3 protein being higher than the reference value, or a subject from which such sample value is obtained, is sometimes referred to herein as being "RBM3 protein high". Further, a sample value of RBM3 protein being lower than, or equal to, the reference value, or a subject from which such sample value is obtained, is sometimes referred to herein as being "RBM3 protein low".

In the context of the present disclosure, the terms "sample value" and "reference value" are to be interpreted broadly. The quantification of RBM3 protein to obtain these values may be done via automatic means, via a scoring system based on visual or microscopic inspection of samples, or via combinations thereof. However, it is also possible for a skilled person, such as a person skilled in the art of histopathology, to determine the sample and reference values by inspection, e.g., of tissue slides that have been prepared and stained for RBM3 protein expression. Determining that the sample value is higher than the reference value may thus correspond to determining, upon visual or microscopic inspection, that a sample tissue slide is more densely stained and/or exhibit a larger fraction of stained cells than a reference tissue slide. The sample value may also be compared to a reference value given by a literal reference, such as a reference value described in wording or by a reference picture. Consequently, the sample and/or reference values may in some cases be mental values that the skilled person determines upon inspection and comparison.

One or more of the steps of the methods of the present disclosure may be implemented in an apparatus. For example, step a) and optionally step b) may be performed in an automatic analysis apparatus, and such apparatus may be based on a platform adapted for immunohistochemical analysis. As an example, one or more tumor tissue sample(s) from the subject in question may be prepared for immunohistochemical analysis manually and then loaded into the automatic analysis apparatus, which gives the sample value of step a) and optionally also performs the comparison with the reference value of step b). The operator performing the analysis, the physician ordering the analysis or the apparatus itself may then draw the conclusion of step c). Consequently, software adapted for drawing the conclusion of step c) may be implemented on the apparatus.

A reference value, found to be relevant for establishing prognosis or making treatment decisions regarding malignant melanoma subjects, for use as comparison with the sample value from the subject, may be provided in various ways. With the knowledge of the teachings of the present disclosure, the skilled artisan can, without undue burden, provide relevant reference values for performing the methods of the present disclosure.

The person performing the methods of the above aspects may, for example, adapt the reference value to desired information. For example, the reference value may be adapted to yield the most significant prognostic information, e.g., the largest separation between the RBM3 protein high survival curve and the RBM3 protein low survival curve (see the figures), which corresponds to the largest difference in survival between the first and the second group of the first aspect. Alternatively, the reference value may be selected such that a group of subjects having particularly good prognoses or particularly poor prognoses is singled out.

In embodiments of the methods of the above aspects, the reference value may correspond to the amount of RBM3 protein expression in a healthy tissue from the subject of the method. As another example, the reference value may be provided by the amount of RBM3 protein expression measured in a standard sample of normal tissue from another, comparable subject. As another example, the reference value may be provided by the amount of RBM3 protein expression measured in a reference sample comprising tumor cells, such as a reference sample of tumor tissue, e.g., malignant melanoma tissue. The amount of protein expression of the reference sample may preferably be previously established. Consequently, the reference value may be provided by the amount of RBM3 protein measured in a reference sample comprising cells expressing a predetermined amount of RBM3 protein.

Further, the reference value may for example be provided by the amount of RBM3 protein expression measured in a reference sample comprising cell lines, such as cancer cell lines, expressing a predetermined, or controlled, amount of RBM3 protein. The person skilled in the art understands how to provide such cell lines, for example guided by the disclosure of Rhodes et al. (2006) *The biomedical scientist*, p 515-520.

Consequently, in embodiments of the methods of the present disclosure, the reference value may be a predetermined value corresponding to the amount of RBM3 protein expression in a reference sample.

However, as discussed further below, the amount of RBM3 protein in the reference sample does not have to directly correspond to the reference value. The reference sample may also provide an amount of RBM3 protein that helps a person performing the method to assess various reference values. For example, the reference sample(s) may help in creating a mental image of the reference value by providing a "positive" reference value and/or a "negative" reference value.

One alternative for the quantification of RBM3 protein expression in a sample, such as the sample earlier obtained from the subject or the reference sample, is the determination of the fraction of cells in the sample that exhibit RBM3 protein expression over a certain level. The fraction may for example be: a "cellular fraction", wherein the RBM3 protein expression of the whole cells is taken into account; a "cytoplasmic fraction", wherein the RBM3 protein expression of only the cytoplasms of the cells is taken into account; or a "nuclear fraction", wherein the RBM3 protein expression of only the nuclei of the cells is taken into account. The nuclear fraction may for example be classified as <2%, 2-25%, >25-75% or >75% immunoreactive cells of the relevant cell population. The "nuclear fraction" corresponds to the percentage of relevant cells in a sample that exhibits a positive staining in the nucleus, wherein a medium or distinct and strong immunoreactivity in the nucleus is considered positive and no or faint immunoreactivity in the nucleus is considered negative. The person skilled in the art of pathology understands which cells that are relevant under the conditions present when performing the method and may determine a nuclear fraction based on his general knowledge and the teachings of the present disclosure. The relevant cells may for example be tumor cells. Further, the skilled artisan understands how to perform corresponding measurements employing the "cytoplasmic fraction" or "cellular fraction".

Another alternative for the quantification of RBM3 protein expression in a sample, such as the sample earlier obtained from the subject or the reference sample, is the determination of the overall staining intensity of the sample. The intensity may for example be: a "cellular intensity", wherein the RBM3 protein expression of the whole cells is taken into account; a "cytoplasmic intensity", wherein the RBM3 protein expression of only the cytoplasms of the cells is taken into account, or a "nuclear intensity", wherein the RBM3 protein expression of only the nuclei of the cells is taken into account. Nuclear intensity is subjectively evaluated in accordance with standards used in clinical histopathological diagnostics. Outcome of a nuclear intensity determination may be classified as: absent=no overall immunoreactivity in the nuclei of relevant cells of the sample, weak=faint overall immunoreactivity in the nuclei of relevant cells of the sample, moderate=medium overall immunoreactivity in the nuclei of relevant cells of the sample, or strong=distinct and strong overall immunoreactivity in the nuclei of relevant cells of the sample. In some embodiments, the weak and moderate values may be combined into a weak/moderate value. The person skilled in the art understands which cells that are relevant under the conditions present when performing the method and may determine a nuclear intensity based on his general knowledge and the teachings of the present disclosure. The relevant cells may for example be tumor cells. Further, the skilled artisan understands how to perform corresponding measurements employing the "cytoplasmic intensity" or "cellular intensity".

The inventors have found that nuclear expression of RBM3 protein is particularly relevant for establishing prognoses.

Thus, in embodiments of the methods of the above aspects, the reference value may be a nuclear fraction, a nuclear intensity or a combination thereof. Accordingly, the sample value may be a nuclear fraction, a nuclear intensity or a combination thereof.

As seen in the figures, more than one reference value based on nuclear expression of RBM3 protein may function as a relevant reference value for determining whether the prognosis is relatively good or relatively poor.

Even though various cut-off:s may be used for dividing a group of malignant melanoma subjects into two different subgroups based on prognosis, lower cut-off:s may be particularly relevant (compare FIGS. 3 and 4).

Thus, in embodiments of the methods of the above aspects, the reference value of step b) is a nuclear fraction of 95% or lower, such as 90 or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

Further, in embodiments of the methods of the above aspects the reference value of step b) may be a moderate nuclear intensity of RBM3 protein expression or lower, such as a weak nuclear intensity of RBM3 protein expression or lower, such as an absent nuclear of RBM3 protein expression.

Also, in embodiments of the methods of the above aspects, the reference value may be a combination or a function of a fraction value and an intensity value. The reference value may thus involve two, and even more, criteria.

In general, the selection of an intensity value and/or a fraction value as the reference value may depend on the staining procedure, e.g., on the type and amount/concentration of the employed antibody and on the type and concentration of the staining reagents.

Guided by the present disclosure, a person skilled in the art, e.g., a pathologist understands how to perform the evaluation yielding a fraction, such as a cellular, cytoplasmic or nuclear fraction, or an intensity, such as a cellular, cytoplasmic or nuclear intensity. For example, the skilled artisan may use a reference sample comprising a predetermined amount of RBM3 protein for establishing the appearance of a certain fraction or intensity.

However, a reference sample may not only be used for the provision of the actual reference value, but also for the provision of an example of a sample with an amount of RBM3 protein that is higher than the amount corresponding to the reference value. As an example, in histochemical staining, such as in immunohistochemical staining, the skilled artisan may use a reference sample for establishing the appearance of a stained sample having a high amount of RBM3 protein, e.g., a positive reference. Subsequently, the skilled artisan may assess the appearances of samples having lower amounts of RBM3 protein, such as the appearance of a sample with an amount of RBM3 protein corresponding to the reference value. In other words, the skilled artisan may use a reference sample to create a mental image of a reference value corresponding to an amount of RBM3 protein which is lower than that of the reference sample. Alternatively, or as a complement, in such assessments, the skilled artisan may use another reference sample having a low amount of RBM3 protein, or lacking detectable RBM3 protein, for establishing the appearance of such sample, e.g., as a "negative reference".

For example, if a moderate nuclear intensity is used as the reference value, two reference samples may be employed: a first reference sample having no detectable RBM3 protein, and thus corresponding to an absent nuclear intensity, which is lower than the reference value; and a second reference sample having an amount of RBM3 protein corresponding to a strong nuclear intensity, which is higher than the reference value.

Consequently, in the evaluation, the skilled artisan may use a reference sample for establishing the appearance of a sample with a high amount of RBM3 protein. Such reference sample may be a sample comprising tissue expressing a high amount of RBM3 protein, such as a sample comprising malignant melanoma tissue having a pre-established high expression of RBM3 protein.

Accordingly, the reference sample may provide an example of a strong nuclear intensity (NI). With the knowledge of the appearance of a sample with strong NI, the skilled artisan may then divide samples into the NI categories absent, weak, moderate and strong. This division may be further assisted by a reference sample lacking detectable RBM3 protein (negative reference), i.e., a reference sample providing an absent nuclear intensity. Also, the reference sample may provide an example of a sample with a nuclear fraction (NF) higher than 75%. With the knowledge of the appearance of a sample with more than 75% positive cells, the skilled artisan may then evaluate the NF of other samples having e.g., a lower percentage of positive cells. This division may be further assisted by a reference sample essentially lacking RBM3 protein (negative reference), i.e., a reference sample providing a low NF (e.g., <5%, such as <2%), or a NF of 0.

As mentioned above, cell lines expressing a controlled amount of RBM3 protein may be used as the reference, in particular as a positive reference.

One or more pictures may also be provided as the "reference sample". For example, such a picture may show an example of a tumor tissue slide stained with a certain antibody during certain conditions and exhibiting a certain nuclear intensity and/or fraction. The above discussion about the "reference sample" applies mutatis mutandis to pictures.

The cell lines or pictures may also form part of the kit according to the present disclosure (see below).

Further, the skilled person should recognize that the usefulness of the methods according to the above aspects is not limited to the quantification of any particular variant of the RBM3 protein present in the subject in question, as long as the protein is encoded by the relevant gene and presents the relevant pattern of expression. As a non-limiting example, the RBM3 protein may comprise a sequence selected from:

i) SEQ ID NO:1; and ii) a sequence which is at least 85% identical to SEQ ID NO:1.

In some embodiments, sequence ii) above is at least 90% identical, at least 91% identical, at least 92% identical, at least 93% identical, at least 94% identical, at least 95% identical, at least 96% identical, at least 97 identical, at least 98% identical or at least 99% identical to SEQ ID NO:1.

As another non-limiting example, the RBM3 protein may comprise, or consists of, a sequence selected from:

i) SEQ ID NO:2; and ii) a sequence which is at least 85% identical to SEQ ID NO:2.

In some embodiments, sequence ii) above is at least 90% identical, at least 91% identical, at least 92% identical, at least 93% identical, at least 94% identical, at least 95% identical, at least 96% identical, at least 97 identical, at least 98% identical or at least 99% identical to SEQ ID NO:2.

The term "% identical", as used in the context of the present disclosure, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). The amino acid residues at each position are compared, and the percentage of positions in the query sequence that have identical correspondences in the target sequence is reported as % identical. Also, the target sequence determines the number of positions that are compared. Consequently, in the context of the present disclosure, a query sequence that is shorter than the target sequence can never be 100% identical to the target sequence. For example, a query sequence of 85 amino acids may at the most be 85% identical to a target sequence of 100 amino acids.

In some embodiments, step a) of the methods of the above aspects may comprise:

obtaining biological material from the subject, excising or selecting a relevant part of the biological material to obtain said sample and optionally arranging the sample on a solid phase to facilitate the evaluation of step a). Step a) may thus, as an example, comprise obtaining malignant melanoma tissue material from the subject, optionally fixating the tissue material in paraffin or formalin, histo-processing the tissue material to obtain a section which constitute said sample and optionally mounting said sample on a transparent slide, such as a glass slide, for microscopy.

In embodiments of the methods of the aspects above, the RBM3 protein may be detected and/or quantified through the application to the sample of a detectable and/or quantifiable affinity ligand, which is capable of selective interaction with the RBM3 protein. The application of the affinity ligand is performed under conditions that enable binding of the affinity ligand to RBM3 protein in the sample.

To concretize, in embodiments of the methods of the aspects above, step a) may comprise:

a1) applying to said sample a quantifiable affinity ligand capable of selective interaction with the RBM3 protein to be evaluated, said application being performed under conditions that enable binding of said affinity ligand to RBM3 protein present in said sample;

a2) removing non-bound affinity ligand; and a3) quantifying the affinity ligand remaining in association with said sample to evaluate said amount.

"Affinity ligand remaining in association with the sample" refers to affinity ligand which was not removed in step a2), e.g., the affinity ligand bound to the sample. Here, the binding may for example be the interaction between antibody and antigen.

However, in some embodiments, the removal of non-bound affinity ligand according to a2), e.g. the washing, is not always necessary. Thus, in some embodiments of the methods of the aspects above, step a) may comprise:

aI) applying to said sample a quantifiable affinity ligand capable of selective interaction with the RBM3 protein to be evaluated, said application being performed under conditions that enable binding of said affinity ligand to RBM3 protein present in said sample;

aII) quantifying the affinity bound to said sample to evaluate said amount.

In the context of the present disclosure, "specific" or "selective" interaction of e.g., an affinity ligand with its target or antigen means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen is from $10^{-7}$ to $10^{-11}$ M. However, high specificity/selectivity does not necessarily require high affinity. Molecules with low affinity (in the molar range) for its counterpart have been shown to be as selective/specific as molecules with much higher affinity. In the case of the present disclosure, a specific or selective interaction refers to the extent to which a particular method can be used to determine the presence and/or amount of a specific protein, the target protein, under given conditions in the presence of other proteins in a tissue sample or fluid sample of a naturally occurring or processed biological fluid. In other words, specificity or selectivity is the capacity to distinguish between related proteins. Specific and selective are sometimes used interchangeably in the present description. For example, the specificity or selectivity of an antibody may be determined as in Examples, Section 2, below, wherein analysis is performed using a protein array set-up, a suspension bead array and a multiplexed competition assay, respectively. Specificity and selectivity determinations are also described in Nilsson P et al. (2005) Proteomics 5:4327-4337.

It is regarded as within the capabilities of those of ordinary skill in the art to select or manufacture the proper affinity ligand and to select the proper format and conditions for detection and/or quantification. Nevertheless, examples of affinity ligands that may prove useful, as well as examples of formats and conditions for detection and/or quantification, are given below for the sake of illustration.

Thus, in embodiments of the present disclosure, the affinity ligand may be selected from the group consisting of antibodies, fragments thereof and derivatives thereof, i.e., affinity ligands based on an immunoglobulin scaffold. The antibodies and the fragments or derivatives thereof may be isolated. Antibodies comprise monoclonal and polyclonal antibodies of any origin, including murine, rabbit, human and other antibodies, as well as chimeric antibodies comprising sequences from different species, such as partly humanized antibodies, e.g., partly humanized mouse antibodies. Polyclonal antibodies are produced by immunization of animals with the antigen of choice. The polyclonal antibodies may be mono-specific. Monoclonal antibodies of defined specificity can be produced using the hybridoma technology developed by Köhler and Milstein (Köhler G and Milstein C (1976) Eur. J. Immunol. 6:511-519). The antibody fragments and derivatives of the present disclosure are capable of selective interaction with the same antigen (e.g. RBM3 protein) as the antibody they are fragments or derivatives of. Antibody fragments and derivatives comprise Fab fragments, consisting of the first constant domain of the heavy chain (CH1), the constant domain of the light chain (CL), the variable domain of the heavy chain (VH) and the variable domain of the light chain (VL) of an intact immunoglobulin protein; Fv fragments, consisting of the two variable antibody domains VH and VL (Skerra A and Plückthun A (1988) Science 240:1038-

1041); single chain Fv fragments (scFv), consisting of the two VH and VL domains linked together by a flexible peptide linker (Bird R E and Walker B W (1991) Trends Biotechnol. 9:132-137); Bence Jones dimers (Stevens F J et al. (1991) Biochemistry 30:6803-6805); camelid heavy-chain dimers (Hamers-Casterman C et al. (1993) Nature 363:446-448) and single variable domains (Cai X and Garen A (1996) Proc. Natl. Acad. Sci. U.S.A. 93:6280-6285; Masat L et al. (1994) Proc. Natl. Acad. Sci. U.S.A. 91:893-896), and single domain scaffolds like e.g., the New Antigen Receptor (NAR) from the nurse shark (Dooley H et al. (2003) Mol. Immunol. 40:25-33) and minibodies based on a variable heavy domain (Skerra A and Plückthun A (1988) Science 240:1038-1041).

In some embodiments, the affinity ligand of the present disclosure is capable of selective interaction with a peptide consisting of the amino acid sequence SEQ ID NO:1. As described below under Examples, Section 1b, the RBM3 fragment SEQ ID NO:1 was designed to lack transmembrane regions to ensure efficient expression in *E. coli*, and to lack any signal peptide, since those are cleaved off in the mature protein. SEQ ID NO:1 was thus designed for immunizations. In addition, the protein fragment was designed to consist of a unique sequence with low homology with other human proteins, to minimize cross reactivity of generated affinity reagents, and to be of a suitable size to allow the formation of conformational epitopes and still allow efficient cloning and expression in bacterial systems. Accordingly, in the cases wherein the affinity ligand is an antibody or fragment o derivative thereof, the affinity ligand may be obtainable by a process comprising a step of immunizing an animal with a peptide whose amino acid sequence consists of the sequence SEQ ID NO:1. For example, the immunization process may comprise primary immunization with the protein in Freund's complete adjuvant. Also, the immunization process may further comprise boosting at least two times, in intervals of 2-6 weeks, with the protein in Freund's incomplete adjuvant. Processes for the production of antibodies or fragments or derivatives thereof against a given target are known in the art.

Further, as described below under Examples, Section 5, two epitope regions (SEQ ID NO:4 and SEQ ID NO:5) have been identified within SEQ ID NO:1. The affinity ligand may thus be obtainable by a process comprising a step of immunizing an animal with a peptide whose amino acid sequence consists of SEQ ID NO:4 or SEQ ID NO:5. Also, the antibody or fragment may be obtainable by a process comprising a step of immunizing an animal with an RBM3 fragment which consists of 20 amino acids or less, such as 15 amino acids or less, and comprises a sequence selected from SEQ ID NO:6-19.

For a further discussion about SEQ ID NO:4-19, see below.

In the context of the present disclosure, a "mono-specific antibody" is one or a population of polyclonal antibodies which has been affinity purified on its own antigen, thereby separating such mono-specific antibodies from other antiserum proteins and non-specific antibodies. This affinity purification results in antibodies that bind selectively to its antigen. In the case of the present disclosure, the polyclonal antisera are purified by a two-step immunoaffinity based protocol to obtain mono-specific antibodies selective for the target protein. Antibodies directed against generic affinity tags of antigen fragments are removed in a primary depletion step, using the immobilized tag protein as the capturing agent. Following the first depletion step, the serum is loaded on a second affinity column with the antigen as capturing agent, in order to enrich for antibodies specific for the antigen (see also Nilsson P et al. (2005) Proteomics 5:4327-4337).

Polyclonal and monoclonal antibodies, as well as their fragments and derivatives, represent the traditional choice of affinity ligands in applications requiring selective biomolecular recognition, such as in the detection and/or quantification of RBM3 protein according to the method aspects above. However, those of skill in the art know that, due to the increasing demand of high throughput generation of selective binding ligands and low cost production systems, new biomolecular diversity technologies have been developed during the last decade. This has enabled a generation of novel types of affinity ligands of both immunoglobulin as well as non-immunoglobulin origin that have proven equally useful as binding ligands in biomolecular recognition applications and can be used instead of, or together with, immunoglobulins.

The biomolecular diversity needed for selection of affinity ligands may be generated by combinatorial engineering of one of a plurality of possible scaffold molecules, and specific/selective affinity ligands are then selected using a suitable selection platform. The scaffold molecule may be of immunoglobulin protein origin (Bradbury A R and Marks J D (2004) J. Immunol. Meths. 290:29-49), of non-immunoglobulin protein origin (Nygren P A and Skerra A (2004) J. Immunol. Meths. 290:3-28), or of an oligonucleotide origin (Gold L et al. (1995) Annu. Rev. Biochem. 64:763-797).

A large number of non-immunoglobulin protein scaffolds have been used as supporting structures in development of novel binding proteins. Non-limiting examples of such structures, useful for generating affinity ligands against RBM3 protein for use according to the present disclosure, are staphylococcal protein A and domains thereof and derivatives of these domains, such as protein Z (Nord K et al. (1997) Nat. Biotechnol. 15:772-777); lipocalins (Beste G et al. (1999) Proc. Natl. Acad. Sci. U.S.A. 96:1898-1903); ankyrin repeat domains (Binz H K et al. (2003) J. Mol. Biol. 332:489-503); cellulose binding domains (CBD) (Smith G P et al. (1998) J. Mol. Biol. 277:317-332; Lehtiö J et al. (2000) Proteins 41:316-322); γ crystallines (Fiedler U and Rudolph R, WO01/04144); green fluorescent protein (GFP) (Peelle B et al. (2001) Chem. Biol. 8:521-534); human cytotoxic T lymphocyte-associated antigen 4 (CTLA-4) (Hufton S E et al. (2000) FEBS Lett. 475:225-231; Irving R A et al. (2001) J. Immunol. Meth. 248:31-45); protease inhibitors, such as Knottin proteins (Wentzel A et al. (2001) J. Bacteriol. 183:7273-7284; Baggio R et al. (2002) J. Mol. Recognit. 15:126-134) and Kunitz domains (Roberts B L et al. (1992) Gene 121:9-15; Dennis M S and Lazarus R A (1994) J. Biol. Chem. 269: 22137-22144); PDZ domains (Schneider S et al. (1999) Nat. Biotechnol. 17:170-175); peptide aptamers, such as thioredoxin (Lu Z et al. (1995) Biotechnology 13:366-372; Klevenz B et al. (2002) Cell. Mol. Life. Sci. 59:1993-1998); staphylococcal nuclease (Norman T C et al. (1999) Science 285: 591-595); tendamistats (McConell S J and Hoess R H (1995) J. Mol. Biol. 250:460-479; Li R et al. (2003) Protein Eng. 16:65-72); trinectins based on the fibronectin type III domain (Koide A et al. (1998) J. Mol. Biol. 284:1141-1151; Xu L et al. (2002) Chem. Biol. 9:933-942); and zinc fingers (Bianchi E et al. (1995) J. Mol. Biol. 247:154-160; Klug A (1999) J. Mol. Biol. 293:215-218; Segal D J et al. (2003) Biochemistry 42:2137-2148).

The above-mentioned examples of non-immunoglobulin protein scaffolds include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

In addition to non-immunoglobulin proteins, oligonucleotides may also be used as affinity ligands. Single stranded nucleic acids, called aptamers or decoys, fold into well-defined three-dimensional structures and bind to their target with high affinity and specificity. (Ellington A D and Szostak J W (1990) Nature 346:818-822; Brody E N and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Plückthun A (1997) Proc. Natl. Acad. Sci. U.S.A. 94:4937-4942), yeast two-hybrid system (Fields S and Song O (1989) Nature 340:245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty P S (2007) Curr Opin Struct Biol 17:474-480, Kronqvist N et al. (2008) Protein Eng Des Sel 1-9, Harvey B R et al. (2004) PNAS 101(25):913-9198), microbead display (Nord O et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

Thus, in embodiments of the present disclosure, the affinity ligand may be a non-immunoglobulin affinity ligand derived from any of the protein scaffolds listed above, or an oligonucleotide molecule.

As mentioned above, the RBM3 protein fragment SEQ ID NO:1 was designed to consist of a unique sequence with low homology with other human proteins and to minimize cross reactivity of generated affinity reagents. Consequently, in embodiments of the present disclosure, the affinity ligand may be capable of selective interaction with a polypeptide consisting of the amino acid sequence SEQ ID NO:1.

As described below under Examples, Section 5, the epitope regions SEQ ID NO:4 and 5 has been identified within SEQ ID NO:1. Thus, in some embodiments, the affinity ligand of the present disclosure is capable of selective interaction with a peptide consisting of an amino acid sequence selected from SEQ ID NO:4 and 5.

As an example, antibodies capable of selective interaction with SEQ ID NO:4 or 5 may be obtained by immunizing an animal with an antigen consisting of the amino acid sequence SEQ ID NO:1 followed by affinity purification of the antisera using peptides consisting of the amino acid sequences SEQ ID NO:4 and SEQ ID NO:5, respectively.

Further, as described above under Examples, Section 6, another four epitope regions (SEQ ID NO:6-9) have been identified. Thus, in some embodiments, the affinity ligand of the present disclosure is capable of selective interaction with an RBM3 fragment which consists of 20 amino acids or less, such as 15 amino acids or less, and comprises a sequence selected from SEQ ID NO:6-9.

Also, as described above under Examples, Section 7, another ten epitope regions (SEQ ID NO:10-19) have been identified. Thus, in some embodiments, the affinity ligand of the present disclosure is capable of selective interaction with an RBM3 fragment which consists of 20 amino acids or less, such as 15 amino acids or less, and comprises a sequence selected from SEQ ID NO:10-19.

Figure 12:
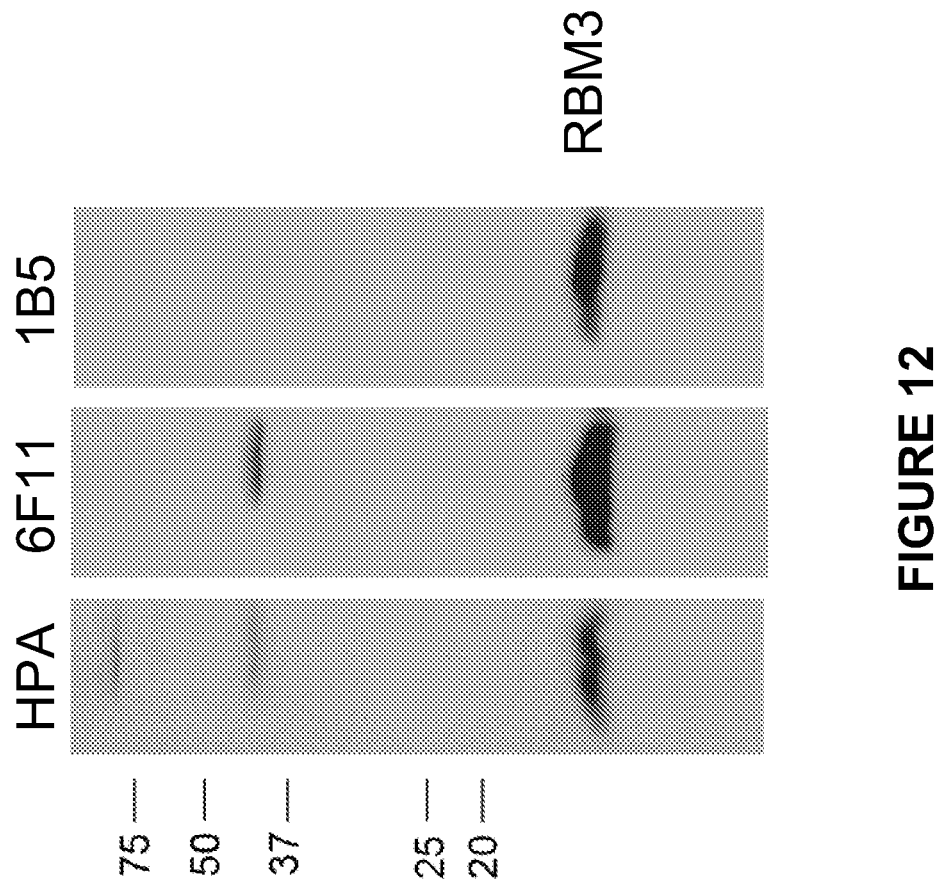
FIG. 12 shows Western blot results for Anti-RBM3, 1B5 and 6F11.

Antibodies having selectivity for a single epitope region (such as monoclonal antibodies) may provide for increased reproducibility in detection analyses as compared to antibodies generated against a longer peptide sequence (such as a PrEST or a full-length protein). The antibodies selective for a single epitope region may also provide for distinct and strong staining in immunohistochemical analyses. These benefits, independently or jointly, may be valuable when establishing prognoses and making decisions regarding treatments according to the present disclosure. In FIG. 12, a benefit (increased selectivity) of monoclonal antibodies according to the present disclosure as compared to a polyclonal antibody is illustrated.

The monoclonal antibodies 6F11 and 1B5 are considered to be particularly beneficial. In FIG. 12, 6F11 and 1B5 are both shown to be more selective than a polyclonal anti-RBM3 antibody. Further, 1B5 is shown to be more selective than 6F11. 1B5 is also employed in Examples, Section 4 below.

SEQ ID NO:17, to which 1B5 is shown to bind in Examples, Section 7, is within SEQ ID NO:5. In preferred embodiments of the present disclosure, the affinity ligand is thus capable of selective interaction with an RBM3 fragment which consists of SEQ ID NO:5, and in particularly preferred embodiments of the present disclosure, the affinity ligand is capable of selective interaction with an RBM3 fragment which consists of 20 amino acids or less, such as 15 amino acids or less, and comprises the sequence SEQ ID NO:17.

6F11 is shown to bind to SEQ ID NO:8 and SEQ ID NO:16. In other preferred embodiments of the present disclosure, the affinity ligand is thus capable of selective interaction with an RBM3 fragment which consists of 20 amino acids or less, such as 15 amino acids or less, and comprises a sequence selected from SEQ ID NO:8 and 16. Note that SEQ ID NO:8 and 16 are overlapping and that such a fragment may comprise the sequences of both SEQ ID NO:8 and 16.

The detection and/or quantification of the affinity ligand capable of selective interaction with the RBM3 protein may be accomplished in any way known to the skilled person for detection and/or quantification of binding reagents in assays based on biological interactions. Accordingly, any affinity ligand described above may be used to quantitatively and/or qualitatively detect the presence of the RBM3 protein. These "primary" affinity ligands may be labeled themselves with various markers or may in turn be detected by secondary, labeled affinity ligands to allow detection, visualization and/or quantification. This can be accomplished using any one or more of a multitude of labels, which can be conjugated to the affinity ligand capable of interaction with RBM3 protein or to any secondary affinity ligand, using any one or more of a multitude of techniques known to the skilled person, and not as such involving any undue experimentation.

Non-limiting examples of labels that can be conjugated to primary and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole) and bioluminescent proteins (e.g., luciferin, luciferase), haptens (e.g., biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g., horseradish peroxidase, alkaline phosphatase, beta-lactamase), radioisotopes (e.g., $^3$H, $^{14}$C, $^{32}$P, $^{35}$S or $^{125}$I)

and particles (e.g., gold). In the context of the present disclosure, "particles" refer to particles, such as metal particles, suitable for labeling of molecules. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) *Curr Opi Biotech.* 13: 40-46). The different types of labels can be conjugated to an affinity ligand using various chemistries, e.g., the amine reaction or the thiol reaction. However, other reactive groups than amines and thiols can be used, e.g., aldehydes, carboxylic acids and glutamine.

The method aspects above may be put to use in any of several known formats and set-ups, of which a non-limiting selection is discussed below.

In a set-up based on histology, the detection, localization and/or quantification of a labeled affinity ligand bound to its RBM3 protein target may involve visualizing techniques, such as light microscopy or immunofluoresence microscopy. Other methods may involve the detection via flow cytometry or luminometry.

Biological material from the subject, such as a surgically removed tumor tissue, may be used for obtaining the sample for detection and/or quantification of RBM3 protein. The sample may thus be an earlier obtained sample. If using an earlier obtained sample in a method, no steps of the method are practiced on the human or animal body. The affinity ligand may be applied to the sample for detection and/or quantification of the RBM3 protein. This procedure enables not only detection of RBM3 protein, but may in addition show the distribution and relative level of expression thereof.

The method of visualization of labels on the affinity ligand may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged affinity ligand may be detected and/or quantified by luminescence developed during a chemical reaction. Detection of an enzymatic reaction is due to a color shift in the sample arising from a chemical reaction. Those of skill in the art are aware that a variety of different protocols can be modified in order for proper detection and/or quantification.

In embodiments of the methods of the above aspects, the sample may be immobilized onto a solid phase support or carrier, such as nitrocellulose or any other solid support matrix capable of immobilizing RBM3 protein present in the biological sample applied to it. Some well-known solid state support materials useful in the present invention include glass, carbohydrate (e.g., Sepharose), nylon, plastic, wool, polystyrene, polyethene, polypropylene, dextran, amylase, films, resins, cellulose, polyacrylamide, agarose, alumina, gabbros and magnetite. After immobilization of the biological sample, primary affinity ligand specific to RBM3 protein may be applied, e.g., as described in Examples, Sections 4, of the present disclosure. If the primary affinity ligand is not labeled in itself, the supporting matrix may be washed with one or more appropriate buffers known in the art, followed by exposure to a secondary labeled affinity ligand and washed once again with buffers to remove unbound affinity ligands. Thereafter, selective affinity ligands may be detected and/or quantified with conventional methods. The binding properties for an affinity ligand may vary from one solid state support to the other, but those skilled in the art should be able to determine operative and optimal assay conditions for each determination by routine experimentation.

Consequently, in embodiments of the methods of the above aspects, the quantifiable affinity ligand of a1) or aI) may be detected using a secondary affinity ligand capable of recognizing the quantifiable affinity ligand. The quantification of a3) or aII) may thus be carried out by means of a secondary affinity ligand with affinity for the quantifiable affinity ligand. As an example, the secondary affinity ligand may be an antibody or a fragment or a derivative thereof.

As an example, one available method for detection and/or quantification of the RBM3 protein is by linking the affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a solid material or with a solid material conjugated to an affinity ligand against the RBM3 protein, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

As stated above, primary and any secondary affinity ligands can be labeled with radioisotopes to enable detection and/or quantification. Non-limiting examples of appropriate radiolabels in the present disclosure are $^3$H, $^{14}$C, $^{32}$P, $^{35}$S or $^{125}$I. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, N.Y., pp 185-196). A thus radiolabeled affinity ligand can be used to visualize RBM3 protein by detection of radioactivity in vivo or in vitro. Radionuclear scanning with e.g., gamma camera, magnetic resonance spectroscopy or emission tomography function for detection in vivo and in vitro, while gamma/beta counters, scintillation counters and radiographies are also used in vitro.

As a fourth aspect of the present disclosure, there is provided a kit for carrying out a method according to the above aspects, which comprises:

a) a quantifiable affinity ligand capable of selective interaction with an RBM3 protein; and b) reagents necessary for quantifying the amount of said quantifiable affinity ligand.

Various components of the kit according to the fourth spect may be selected and specified as described above in connection with the method aspects of the present disclosure.

Thus, the kit according to the present disclosure comprises an affinity ligand against an RBM3 protein, as well as other means that help to quantify the specific and/or selective affinity ligand after it has bound specifically and/or selectively to the RBM3 protein. For example, the kit may contain a secondary affinity ligand for detecting and/or quantifying a complex formed by the RBM3 protein and the affinity ligand capable of selective interaction with the RBM3 protein. The kit may also contain various auxiliary substances other than affinity ligands, to enable the kit to be used easily and efficiently. Examples of auxiliary substances include solvents for dissolving or reconstituting lyophilized protein components of the kit, wash buffers, substrates for measuring enzyme activity in cases where an enzyme is used as a label, target retrieval solution to enhance the accessibility to antigens in cases where paraffin or formalin-fixed tissue samples are used, and substances such as reaction arresters, e.g., endogenous enzyme block solution to decrease the background staining and/or counterstaining solution to increase staining contrast, that are commonly used in immunoassay reagent kits.

In embodiments of the kit aspect, the affinity ligand may be any one of the affinity ligands described above in connection with the method aspects.

Further, in accordance with what is described above in connection with the method aspects, the detectable affinity ligand may in embodiments of the kit aspect comprise a label selected from the group consisting of fluorescent dyes and metals, chromophoric dyes, chemiluminescent compounds and bioluminescent proteins, enzymes, radioisotopes, particles and quantum dots. Alternatively, the reagents necessary for quantifying the amount of the affinity ligand comprise a secondary affinity ligand capable of recognizing the quantifiable affinity ligand. As an example, the secondary affinity ligand capable of recognizing the quantifiable affinity ligand comprises a label selected from the group consisting of fluorescent dyes or metals, chromophoric dyes, chemiluminescent compounds and bioluminescent proteins, enzymes, radioisotopes, particles and quantum dots.

The kit according to the kit aspect may also advantageously comprise a reference sample for provision of, or yielding, the reference value to be used for comparison with the sample value. For example, the reference sample may comprise a predetermined amount of RBM3 protein. Such a reference sample may for example be constituted by a tissue sample containing the predetermined amount of RBM3 protein. The tissue reference sample may then be used by the person of skill in the art in the determination of the RBM3 expression status in the sample being studied, by manual, such as ocular, or automated comparison of expression levels in the reference tissue sample and the subject sample. As another example, the reference sample may comprise cell lines, such as cancer cell lines, expressing a predetermined, or controlled, amount of RBM3 protein. The person skilled in the art understands how to provide such cell lines, for example guided by the disclosure of Rhodes et al. (2006) The biomedical scientist, p 515-520. As an example, the cell lines may be formalin fixed. Also, such formalin fixed cell lines may be paraffin embedded.

The wording "reference sample for provision of the reference value" is to be interpreted broadly in the context of the present disclosure. The reference sample may comprise an amount of RBM3 protein actually corresponding to the reference value, but it may also comprise an amount of RBM3 protein corresponding to a value being higher than the reference value. In the latter case, the "high" value may be used by a person performing the method as an upper reference (positive reference) for assessing, e.g., the appearance of, a reference value which is lower than the "high" value. The person skilled in the art of immunohistochemistry understands how to do such an assessment. Further, as an alternative or a complementing example, the skilled person may use another reference sample comprising a low amount of RBM3 protein for provision of a "low" value in such an assessment, e.g., as a negative reference. This is further discussed above in connection with the method aspects.

Consequently, in embodiments of the kit aspect, the reference sample may comprise an amount of RBM3 protein corresponding to the reference value. As an example, the reference sample may comprise an amount of RBM3 protein corresponding to a nuclear fraction of 95% or lower, such as 90% or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

Alternatively, or as a complement, the reference sample may comprise an amount of RBM3 protein corresponding to a moderate nuclear intensity expression or lower, such as a weak nuclear intensity of RBM3 protein expression or lower, such as an absent nuclear intensity.

The provision of fraction values and intensity values is discussed above in connection with the method aspects.

Further, in alternative or complementing embodiments of the kit aspect, the kit may comprise a reference sample comprising an amount of RBM3 protein corresponding to a value being higher than the reference value. In these embodiments, the reference sample may for example comprise an amount of RBM3 protein corresponding to a nuclear fraction of 75% or higher and/or a strong nuclear intensity.

In other alternative or complementing embodiments of the kit aspect, the kit may comprise a reference sample comprising an amount of RBM3 protein corresponding to a value being lower than or equal to the reference value, e.g., an absent nuclear intensity and/or a nuclear fraction of <2% RBM3 protein positive cells, such as 0% RBM3 protein positive cells.

The kit may thus comprise: a reference sample comprising an amount of RBM3 protein corresponding to a predetermined reference value; a reference sample comprising an amount of RBM3 protein corresponding to a value being higher than a predetermined reference value; and/or a reference sample comprising an amount of RBM3 protein corresponding to a value being lower than or equal to a predetermined reference value.

Consequently, embodiments of the kit may comprise: a first reference sample comprising an amount of RBM3 protein being higher than a predetermined reference value; and a second reference sample comprising an amount of RBM3 protein being lower than or equal to the predetermined reference value.

In embodiments of the kit aspect, the reference sample may be a tissue sample, such as a tissue sample adapted to ocular or microscopic evaluation. As an example, the tissue reference sample may be fixated in paraffin or buffered formalin and/or histo-processed to sections (e.g., µm-thin sections) that are mounted on microscopic glass-slides. The tissue reference sample may be further adapted to staining with affinity ligands, such as antibodies, against an RBM3 protein.

Consequently, in embodiments of the kit aspect, the reference sample may be adapted to directly, or indirectly, provide any relevant reference value, such as any one of the reference values discussed above.

Further embodiments of the reference sample of the kit aspect are discussed above in connection with the reference values and reference samples of the method aspects.

Following the findings presented above, the inventors have realized several uses for the RBM3 protein and fragments thereof.

Thus, as a fifth aspect of the present disclosure, there is provided an RBM3 protein fragment which consists of 50 amino acids or less and comprises a sequence selected from SEQ ID NO:4-19.

In embodiments of the fifth aspect, the fragment consists of 29 amino acids or less.

In further embodiments of the fifth aspect, the fragment consists of 20 amino acids or less, such as 15 amino acids or less, and comprises a sequence selected from SEQ ID NO:6-19.

Possible uses of such fragments are described below.

As a first configuration of a sixth aspect of the present disclosure, there is provided a use of an RBM3 protein as a prognostic marker for a mammalian subject having a malignant melanoma.

In a similar manner, there is provided a use of an RBM3 protein, such as RBM3 protein in a sample, as a marker of a relatively good prognosis for a mammalian subject having a malignant melanoma.

The sample of the sixth aspect may be any sample from the subject, preferably a tissue sample from the primary tumor.

The use of the first configuration may be entirely in vitro, e.g., on previously obtained samples.

In the context of the present disclosure, "prognostic marker" refers to something material which presence indicates a prognosis. The marker may thus be a biomarker, such as a human protein.

As a second configuration of the sixth aspect, there is provided a use of an RBM3 protein, or an antigenically active fragment thereof, for the production, selection or purification of a prognostic agent for a mammalian subject having a malignant melanoma.

The selection and purification may be in vitro, while the production may be in vivo.

In the context of the present disclosure, "prognostic agent" refers to an agent having at least one property being valuable in an establishment of a prognosis, e.g., a prognosis for a mammalian subject having a malignant melanoma. For example, the prognostic agent may be capable of selective interaction with the prognostic marker.

The prognostic agent may be an affinity ligand capable of selective interaction with the RBM3 protein or the antigenically active fragment thereof. Examples of such affinity ligands are discussed above in connection with the method aspects.

Guided by the teachings of the present disclosure, the person skilled in the art understands how to use the RBM3 protein or fragment in the production, selection or purification of the prognostic agent. For example, the use may comprise affinity purification on a solid support onto which the RBM3 protein has been immobilized. The solid support may for example be arranged in a column. Further, the use may comprise selection of affinity ligands having specificity for the RBM3 protein using a solid support onto which the polypeptide has been immobilized. Such solid support may be well plates (such as 96 well plates), magnetic beads, agarose beads or sepharose beads. Further, the use may comprise analysis of affinity ligands on a soluble matrix, for example using a dextran matrix, or use in a surface plasmon resonance instrument, such as a Biacore™ instrument, wherein the analysis may for example comprise monitoring the affinity for the immobilized RBM3 protein of a number of potential affinity ligands.

Also, for the production of the prognostic agent, the RBM3 protein or an antigenically active fragment thereof may be used in an immunization of an animal, such as a rabbit or mouse.

Such use may be involved in a method comprising the steps:
i) immunizing an animal using the RBM3 protein or antigenically an active fragment thereof as the antigen;
ii) obtaining serum comprising the prognostic agent from the immunized animal; and, optionally,
iii) isolating the prognostic agent from the serum.

Alternatively the steps following the first step may be:
ii') obtaining cells from the immunized animal, which cells comprise DNA encoding the endocrine treatment indicating agent,
iii') fusing the cells with myeloma cells to obtain at least one clone, and
iv') obtaining the prognostic agent expressed by the clone.

In embodiments of the sixth aspect, the amino acid sequence of the RBM3 protein may comprise a sequence selected from:
i) SEQ ID NO:1; and
ii) a sequence which is at least 85% identical to SEQ ID NO:1.

In some embodiments, sequence ii) is at least 90% identical, at least 91% identical, at least 92% identical, at least 93% identical, at least 94 identical, at least 95% identical, at least 96% identical, at least 97 identical, at least 98% identical or at least 99% identical to SEQ ID NO:1.

Further, in embodiments of the sixth aspect the amino acid sequence of the RBM3 protein may comprise or consist of a sequence selected from:
i) SEQ ID NO:2; and
ii) a sequence which is at least 85% identical to SEQ ID NO:2.

In some embodiments, sequence ii) is at least 90% identical, at least 91% identical, at least 92% identical, at least 93% identical, at least 94 identical, at least 95% identical, at least 96% identical, at least 97 identical, at least 98% identical or at least 99% identical to SEQ ID NO:2.

The antigenically active fragment of the sixth aspect may for example be any one of the fragments of the fifth aspect.

As a seventh aspect of the present disclosure, there is provided an affinity ligand capable of selective interaction with a RBM3 protein.

Different embodiments of such an affinity ligand are discussed above in connection with the method aspects.

As an eighth aspect of the present disclosure, there is provided a use of an affinity ligand according to the seventh aspect as prognostic agent for a mammalian subject having a malignant melanoma. Consequently, the affinity ligand may be used for establishing a prognosis for a malignant melanoma subject. Such use may for example be performed in vitro, e.g., involving the determination of the amount of RBM3 in at least part of a sample earlier obtained from the subject.

In an equivalent manner, it is provided a use of the affinity ligand in the manufacture of a prognostic agent for establishing a prognosis for a mammalian subject having a malignant melanoma.

Examples

Polyclonal Antibodies

1. Generation of Antigen
a) Materials and Methods

A suitable fragment of the target protein encoded by the EnsEMBL Gene ID ENSG00000102317 was selected using bioinformatic tools with the human genome sequence as template (Lindskog M et al (2005) Biotechniques 38:723-727, EnsEMBL, www.ensembl.org). The fragment was used as template for the production of a 134 amino acid long fragment corresponding to amino acids 18-151 (SEQ ID NO:1) of the RBM3 protein (SEQ ID NO:2; EnsEMBL entry no. ENSP00000365946).

A fragment of the RBM3 gene transcript containing nucleotides 281-682, of EnsEMBL entry number ENST00000376755 (SEQ ID NO:3), was isolated by a Superscript™ One-Step RT-PCR amplification kit with Platinum® Taq (Invitrogen) and a human total RNA pool panel as template (Human Total RNA, BD Biosciences Clontech). Flanking restriction sites NotI and AscI were introduced into the fragment through the PCR amplification primers, to allow in-frame cloning into the expression vector (forward primer: GACGAGCAGGCACTGGAAG (SEQ ID NO:20), reverse primer: GTAATTTCCTCCTGAGTAGC (SEQ ID NO:21). Then, the downstream primer was biotinylated to allow solid-phase cloning as previously described, and the resulting biotinylated PCR product was immobilized onto Dynabeads M280 Streptavidin (Dynal Biotech) (Larsson M et al (2000) J. Biotechnol. 80:143-157). The fragment was released from the solid support by NotI-AscI digestion (New England Biolabs), ligated into the pAff8c vector (Larsson M et al, supra) in frame with a dual affinity tag consisting of a hexahistidyl tag for immobilized metal ion chromatography (IMAC) purification and an immunopotentiating albumin binding protein (ABP) from streptococcal protein G (Sjölander A et al (1997) J. Immunol. Methods 201:115-123; Ståhl S et al (1999) Encyclopedia of Bioprocess Technology: Fermentation, Biocatalysis and Bioseparation (Fleckinger M C and Drew S W, eds) John Wiley and Sons Inc., New York, pp 49-63), and transformed into $E.$ $coli$ BL21(DE3) cells (Novagen). The sequences of the clones were verified by dye-terminator cycle sequencing of plasmid DNA amplified using TempliPhi DNA sequencing amplification kit (GE Healthcare, Uppsala, Sweden) according to the manufacturer's recommendations.

BL21(DE3) cells harboring the expression vector were inoculated in 100 ml 30 g/l tryptic soy broth (Merck KGaA) supplemented with 5 g/l yeast extract (Merck KGaA) and 50 mg/l kanamycin (Sigma-Aldrich) by addition of 1 ml of an overnight culture in the same culture medium. The cell culture was incubated in a 1 liter shake flask at 37° C. and 150 rpm until the optical density at 600 nm reached 0.5-1.5. Protein expression was then induced by addition of isopropyl-β-D-thiogalactopyranoside (Apollo Scientific) to a final concentration of 1 mM, and the incubation was continued overnight at 25° C. and 150 rpm. The cells were harvested by centrifugation at 2400 g, and the pellet was re-suspended in 5 ml lysis buffer (7 M guanidine hydrochloride, 47 mM $Na_2HPO_4$, 2.65 mM $NaH_2PO_4$, 10 mM Tris-HCl, 100 mM NaCl, 20 mM β-mercaptoethanol; pH=8.0) and incubated for 2 hours at 37° C. and 150 rpm. After centrifugation at 35300 g, the supernatant containing the denatured and solubilized protein was collected.

The $His_6$-tagged fusion protein was purified by immobilized metal ion affinity chromatography (IMAC) on columns with 1 ml Talon® metal ($Co^{2+}$) affinity resin (BD Biosciences Clontech) using an automated protein purification procedure (Steen J et al (2006) Protein Expr. Purif. 46:173-178) on an ASPEC XL4™ (Gilson). The resin was equilibrated with 20 ml denaturing washing buffer (6 M guanidine hydrochloride, 46.6 mM $Na_2HPO_4$, 3.4 mM $NaH_2PO_4$, 300 mM NaCl, pH 8.0-8.2). Clarified cell lysates were then added to the column. Thereafter, the resin was washed with a minimum of 31.5 ml washing buffer prior to elution in 2.5 ml elution buffer (6 M urea, 50 mM $NaH_2PO_4$, 100 mM NaCl, 30 mM acetic acid, 70 mM Na-acetate, pH 5.0). The eluted material was fractioned in three pools of 500, 700 and 1300 µl. The 700 µl fraction, containing the antigen, and the pooled 500 and 1300 µl fractions were stored for further use.

The antigen fraction was diluted to a final concentration of 1 M urea with phosphate buffered saline (PBS; 1.9 mM $NaH_2PO_4$, 8.1 mM $Na_2HPO_4$, 154 mM NaCl) followed by a concentration step to increase the protein concentration using Vivapore 10/20 ml concentrator with molecular weight cut off at 7500 Da (Vivascience AG). The protein concentration was determined using a bicinchoninic acid (BCA) micro assay protocol (Pierce) with a bovine serum albumin standard according to the manufacturer's recommendations. The protein quality was analyzed on a Bioanalyzer instrument using the Protein 50 or 200 assay (Agilent Technologies).

b) Results

A gene fragment corresponding to nucleotides 281-682 of the full-lengths transcript of RBM3 (SEQ ID NO:3) was successfully isolated by RT-PCR from a human RNA pool using primers specific. The fragment codes for amino acids 18 to 151 of the target protein RBM3 (SEQ ID NO:2). The 134 amino acid fragment (SEQ ID NO:1) of the target protein (SEQ ID NO:2) was designed to lack transmembrane regions to ensure efficient expression in $E.$ $coli$, and to lack any signal peptide, since those are cleaved off in the mature protein. In addition, the protein fragment was designed to consist of a unique sequence with low homology with other human proteins, to minimize cross reactivity of generated affinity reagents, and to be of a suitable size to allow the formation of conformational epitopes and still allow efficient cloning and expression in bacterial systems.

A clone encoding the correct amino acid sequence was identified, and, upon expression in $E.$ $coli$, a single protein of the correct size was produced and subsequently purified using immobilized metal ion chromatography. After dilution of the eluted sample to a final concentration of 1 M urea and concentration of the sample to 1 ml, the concentration of the protein fragment was determined to be 10.4 mg/ml and was 96.0% pure according to purity analysis.

2. Generation of Antibodies a) Materials and Methods

The purified RBM3 fragment as obtained above was used as antigen to immunize a rabbit in accordance with the national guidelines (Swedish permit no. A 84-02). The rabbit was immunized intramuscularly with 200 µg of antigen in Freund's complete adjuvant as the primary immunization, and boosted three times in four week intervals with 100 µg antigen in Freund's incomplete adjuvant.

Antiserum from the immunized animal was purified by a three-step immunoaffinity based protocol (Agaton C et al (2004) J. Chromatogr. A 1043:33-40; Nilsson P et al (2005) Proteomics 5:4327-4337). In the first step, 7 ml of total antiserum was buffered with 10×PBS to a final concentration of 1×PBS (1.9 mM $NaH_2PO_4$, 8.1 mM $Na_2HPO_4$, 154 mM NaCl), filtered using a 0.45 µm pore-size filter (Acrodisc®, Life Science) and applied to an affinity column containing 5 ml N-hydroxysuccinimide-activated Sepharose™ 4 Fast Flow (GE Healthcare) coupled to the dual affinity tag protein $His_6$-ABP (a hexahistidyl tag and an albumin binding protein tag) expressed from the pAff8c vector and purified in the same way as described above for the antigen protein fragment. In the second step, the flow-through, depleted of antibodies against the dual affinity tag $His_6$-ABP, was loaded at a flow rate of 0.5 ml/min on a 1 ml Hi-Trap NHS-activated HP column (GE Healthcare) coupled with the RBM3 protein fragment used as antigen for immunization (SEQ ID NO:1). The $His_6$-ABP protein and the protein fragment antigen were coupled to the NHS activated matrix as recommended by the manufacturer. Unbound material was washed away with 1×PBST (1×PBS, 0.1% Tween20, pH 7.25), and captured antibodies were eluted using a low pH glycine buffer (0.2 M glycine, 1 mM EGTA, pH 2.5). The eluted antibody fraction was collected automatically, and loaded onto two 5 ml HiTrap™ desalting columns (GE Healthcare) connected in series for efficient buffer exchange in the third step. The second and third purification steps were run on the ÄKTAxpress™ platform (GE Healthcare). The antigen selective (mono-specific) antibodies (msAbs) were eluted with PBS buffer, supplemented with glycerol and NaN$_3$ to final concentrations of 40% and 0.02%, respectively, for long term storage at −20° C. (Nilsson P et al (2005) Proteomics 5:4327-4337).

The specificity and selectivity of the affinity purified antibody fraction were analyzed by binding analysis against the antigen itself and against 94 other human protein fragments in a protein array set-up (Nilsson P et al (2005) Proteomics 5:4327-4337). The protein fragments were diluted to 40 µg/ml in 0.1 M urea and 1×PBS (pH 7.4) and 50 µl of each were transferred to the wells of a 96-well spotting plate. The protein fragments were spotted in duplicate and immobilized onto epoxy slides (SuperEpoxy, TeleChem) using a pin-and-ring arrayer (Affymetrix 427). The slide was washed in 1×PBS (5 min) and the surface was then blocked (SuperBlock®, Pierce) for 30 minutes. An adhesive 16-well silicone mask (Schleicher & Schuell) was applied to the glass before the mono-specific antibodies were added (diluted 1:2000 in 1×PBST to appr. 50 ng/ml) and incubated on a shaker for 60 min. Affinity tag-specific IgY antibodies were co-incubated with the mono-specific antibodies in order to quantify the amount of protein in each spot. The slide was washed with 1×PBST and 1×PBS twice for 10 min each. Secondary antibodies (goat anti-rabbit antibody conjugated with Alexa 647 and goat anti-chicken antibody conjugated with Alexa 555, Molecular Probes) were diluted 1:60000 to 30 ng/ml in 1×PBST and incubated for 60 min. After the same washing procedure, as for the first incubation, the slide was spun dry and scanned (G2565BA array scanner, Agilent), thereafter images were quantified using image analysis software (GenePix 5.1, Axon Instruments).

In addition, the specificity and selectivity of the affinity-purified antibody were analyzed by Western blot. Western blot was performed by separation of total protein extracts from selected human cell lines on pre-cast 10-20% SDS-PAGE gradient gels (Bio-Rad Laboratories) under reducing conditions, followed by electro-transfer to PVDF membranes (Bio-Rad Laboratories) according to the manufacturer's recommendations. The membranes were blocked (5% dry milk, 1×TBST; 0.1 M Tris-HCl, 0.5 M NaCl, 0.1% Tween20) for 1 h at room temperature, incubated with the primary affinity purified antibody (diluted 1:500 in blocking buffer) and washed in TBST. The secondary HRP-conjugated antibody (swine anti-rabbit immunoglobulin/HRP, DakoCytomation) was diluted 1:3000 in blocking buffer and chemiluminescence detection was carried out using a Chemidoc™ CCD camera (Bio-Rad Laboratories) and SuperSignal® West Dura Extended Duration substrate (Pierce), according to the manufacturer's protocol.

b) Results

The quality of polyclonal antibody preparations has proven to be dependent on the degree of stringency in the antibody purifications, and it has previously been shown that depletion of antibodies directed against epitopes not originated from the target protein is necessary to avoid cross-reactivity to other proteins and background binding (Agaton C et al (2004) J. Chromatogr. A 1043:33-40). Thus, a protein microarray analysis was performed to ensure that mono-specific polyclonal antibodies of high specificity had been generated by depletion of antibodies directed against the His$_6$-tag as well as of antibodies against the ABP-tag.

To quantify the amount of protein in each spot of the protein array, a two-color dye labeling system was used, with a combination of primary and secondary antibodies. Tag-specific IgY antibodies generated in hen were detected with a secondary goat anti-hen antibody labeled with Alexa 555 fluorescent dye. The specific binding of the rabbit msAb to its antigen on the array was detected with a fluorescently Alexa 647 labeled goat anti-rabbit antibody. Each protein fragment was spotted in duplicates. The protein array analysis shows that the affinity purified mono-specific antibody against RBM3 is highly selective to the correct protein fragment and has a very low background to all other protein fragments analyzed on the array.

The result of the Western blot analysis shows that the antibody specifically detects a single band of approximately 16 kDa in two breast tumor cell lines, T47D and MCF-7. The theoretical molecular weight of RBM3 is 16 kDa (as calculated from the RBM3 amino acid sequence SEQ ID NO:2), corresponding well to the result obtained.

Monoclonal Antibodies

3. Generation of Monoclonal Antibodies.

a) Materials and Methods

The purified fragment (SEQ ID NO:1) obtained in Section 1 was used as antigen for production of monoclonal antibodies. Antigen was sent to AbSea Biotechnology Ltd (Beijing, China) and briefly, the antigen was injected subcutaneously into BALB/c mice (4-6 weeks old, female) at three week intervals. The antigen was mixed with complete Freund's adjuvant for the first injection and incomplete Freund's adjuvant for the following injections. Three days before fusion, the mouse was last challenged with antigen intravenously. Hybridomas were generated by fusion of mouse splenocytes with the Sp2/0 myeloma cell line. By screening several cell lines using ELISA, cells that secreted antibodies specific for the antigen (SEQ ID NO:1) were identified and delivered to Atlas Antibodies AB for further characterization. Cell lines that showed positive results in ELISA, Western blot (WB) and immunohistochemistry (IHC) were selected for subcloning, performed by AbSea Biotechnology Ltd.

In addition, the immunohistochemical staining patterns of the monoclonal antibodies were compared to that of the polyclonal anti-RBM3 antibody generated in Section 2. This polyclonal antibody is sometimes referred to herein as "anti-RBM3".

b) Results

Cell-lines were screened by ELISA (at AbSea) to identify lines that produce monoclonal antibodies (mAbs) that recognize the antigen (SEQ ID NO:1), but not the affinity tag His-ABP. Eight cell-lines showed specific binding to the antigen SEQ ID NO:1 in ELISA and were selected for further testing. For each of the selected eight clones 150-300 µl supernatant was collected, azide was added, and the supernatants were delivered to Atlas Antibodies AB on wet ice. The supernatants were stored at +4° C. upon arrival according to the instructions from AbSea. Further testing of the cell lines resulted in the identification of three interesting cell lines, clones 1B5, 6F11 and 7G3 that gave positive results in both Western blot and IHC analysis. These clones were selected for subcloning and expansion, performed by AbSea Biotechnology Ltd.

Tissue Micro Array (TMA) Analysis

4. Malignant Melanoma Cohort
a) Material and Methods

Archival formalin-fixed paraffin-embedded tissues from a patient cohort consisting of 157 patients surgically treated for primary cutaneous malignant melanoma were collected from the Department of Pathology, Uppsala University Hospital, Uppsala, Sweden. Patients were diagnosed between 1982 and 2004. Ethical permission was obtained from the Research Ethics Committee at Uppsala University, Uppsala, Sweden.

T-stage (according to UICC 2002) was recorded for all specimens: 64 tumors were stage I, 34 tumors were stage II, 31 stage III and 17 stage IV, 5 of the patients had distant metastases and were staged M1. For 6 patients information on stage was lacking. Recurrence in the form of metastases was registered: 41 patients had metastases and 74 patients did not. For 4 patients information on recurrence was lacking. The cohort included 96 cases of SSM, 47 NMM, 6 ALM, 4 LMM, 1 Desmoplastic, 2 unclassified, and 1 malignant melanoma in situ. Median follow-up time was 77 months.

All 157 cases were histopathologically re-evaluated on slides stained with hematoxylin and eosin. TMA:s were then constructed by sampling 2×1.0 mm cores per case from areas representative of malignant melanoma.

The material was analyzed according to the following method using both the polyclonal antibody produced according to Section 2 above (Anti-RBM3, HPA003624) and the monoclonal antibody 1B5 produced according to Section 3 above. Automated immunohistochemistry was performed as previously described (Kampf C et al (2004) Clin. Proteomics 1:285-300). In brief, the glass slides were incubated for 45 min in 60° C., de-paraffinized in xylene (2×15 min) and hydrated in graded alcohols. For antigen retrieval, slides were immersed in TRS (Target Retrieval Solution, pH 6.0, Dako, Copenhagen, Denmark) and boiled for 4 min at 125° C. in a Decloaking Chamber® (Biocare Medical). Slides were placed in the Autostainer® (Dako) and endogenous peroxidase was initially blocked with $H_2O_2$ (Dako). The slides were incubated for 30 min at room temperature with primary RBM3 antibody (Anti-RBM3 or 1B5). This was followed by incubation for 30 min at room temperature with goat anti-rabbit peroxidase conjugated Envision®. Between all steps, slides were rinsed in wash buffer (Dako). Finally, diaminobenzidine (Dako) was used as chromogen and Harris hematoxylin (Sigma-Aldrich) was used for counterstaining. The slides were mounted with Pertex® (Histolab).

All samples of immunohistochemically stained tissue were manually evaluated under the microscope and annotated by a certified pathologist. Annotation of each sample was performed using a simplified scheme for classification of IHC outcome. Each tissue sample was examined for representativity and immunoreactivity.

Basic annotation parameters included an evaluation of subcellular localization (nuclear expression and/or cytoplasmic expression), staining intensity and fraction of stained cells. Staining intensity was subjectively evaluated in accordance to standards used in clinical histo-pathological diagnostics and outcome was classified as: absent=no immunoreactivity, weak=faint immunoreactivity, moderate=medium immunoreactivity, or strong=distinct and strong immunoreactivity. Also fraction of stained cells was subjectively evaluated in accordance to standards used in clinical histo-pathological diagnostics and outcome was classified according to the percentage immunoreactive cells of the relevant cell population. The skilled artisan will recognize that this annotation procedure is similar to a calculation of an Allred score, see e.g. Allred et al (1998) Mod Pathol 11(2), 155.

For statistical analyses, the nuclear fraction (NF) and nuclear intensity (NI) were evaluated. Based on the survival trends for individual strata, dichotomized variables were constructed for further statistical analyses. For analysis of polyclonal anti-RBM3, a high nuclear fraction was defined as >1% (NF>0) of cells stained and a low nuclear fraction was defined as 0-1% (NF=0) of cells stained. Also, a high nuclear fraction of >75% (NF=3) was used as an alternative cut-off. Further, a high protein expression level was defined as a weak, moderate or strong nuclear intensity (NI>0) and a low protein expression level was defined as an absent nuclear intensity (NI=0). The monoclonal antibody 1B5, stained stronger and for these analyses a high nuclear fraction was defined as >75% (NF=3) of cells stained and a low nuclear fraction was defined as 0-75% (NF<3) of cells stained. Further, a high protein expression level was defined as a moderate or strong nuclear intensity (NI>1) and a low protein expression level was defined as an absent or weak nuclear intensity (NI≤1).

The above classification of samples was used to estimate disease free survival (DFS) and overall survival (OS) according to the Kaplan-Meier estimator, and the log-rank test was used to compare survival in different strata. All statistical tests were two-sided, and p-values of <0.05 were considered significant. All calculations were made with the statistical package SPSS 17.0 (SPSS Inc. Illinois, USA).

b) Results

Figure 1B:
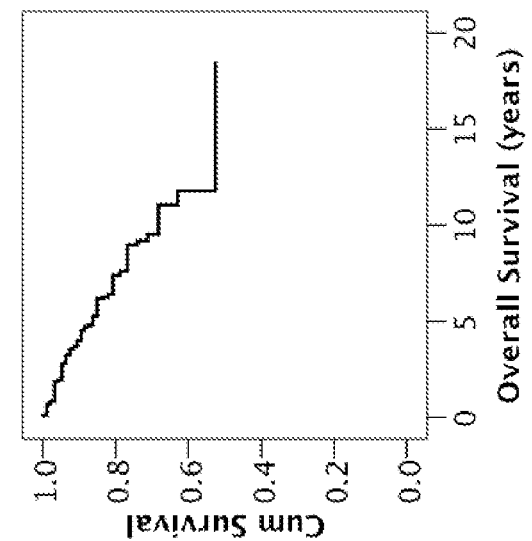
FIG. 1B shows OS for the 63 SMM patients and FIG. 1C shows OS for the 44 NMM patients. Estimated five-year survival is approximately 79%, 85% and 63%, respectively.
Figure 1C:
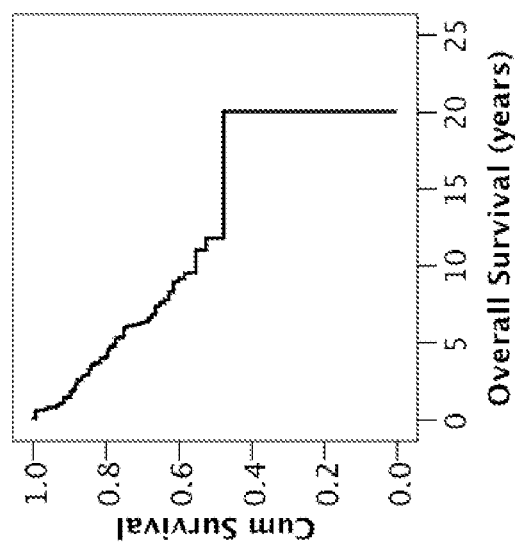
Figures 2A, 2B, 2C:
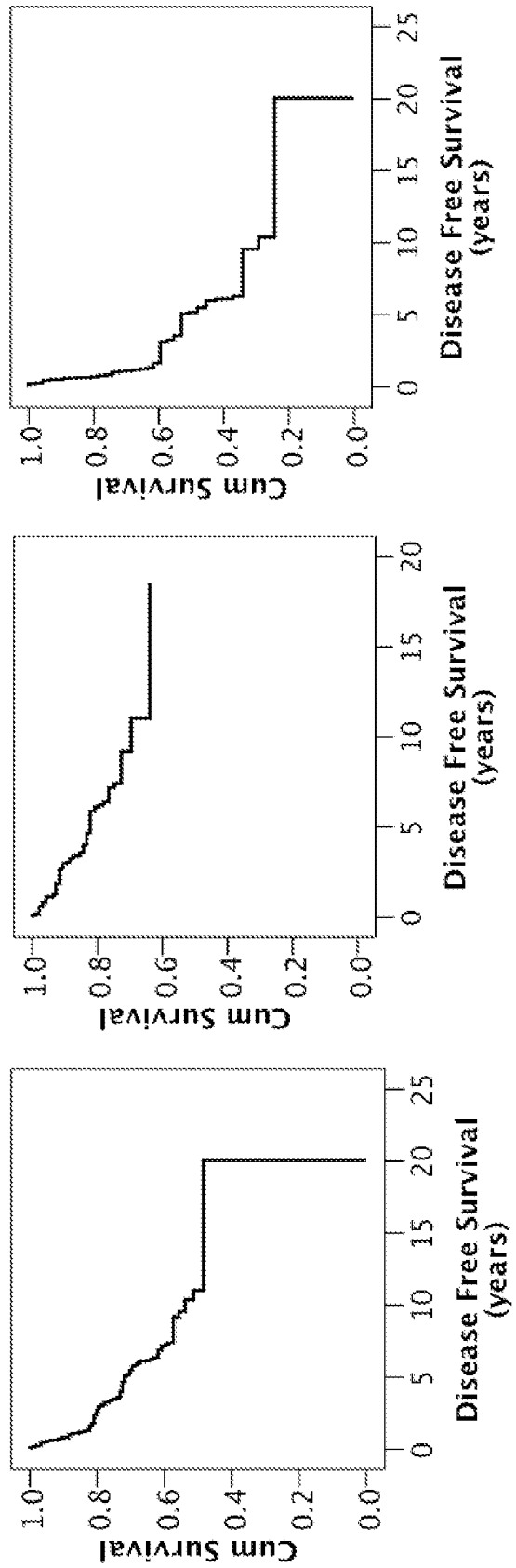
FIG. 2A shows DFS for all 119 patients.
FIG. 2B shows DFS for the 63 SMM patients and FIG. 2C shows DFS for the 44 NMM patients. Estimated five-year survival is approximately 72%, 81% and 53%, respectively.

Initial analysis of the cohort revealed that five-year OS for all patients was approximately 79% and for the subgroups SSM and NMM approximately 85% and 63%, respectively (FIG. 1A-C). Five-year DFS was approximately 72% for all patients and approximately 81% and 53% for SMM and NMM, respectively, as seen in FIG. 2A-C.

Immunohistochemical analysis of RBM3 expression with anti-RBM3 could be performed on 119 of the 157 tumor samples. A positive nuclear fraction (NF>0) was observed in 102 of the 119 tissue cores (86%). Tumor cells with a nucleic staining (NI>0) were observed in 103 of the 119 subjects (87%).

Immunohistochemical analysis of RBM3 expression with 1B5 could be performed on 120 of the 157 tumor samples. A positive nuclear fraction (NF>0) was observed in 117 of the 120 tissue cores (87%). Tumor cells with a nucleic staining (NI>0) were observed in 119 of the 120 subjects (99%).

Figure 3B:
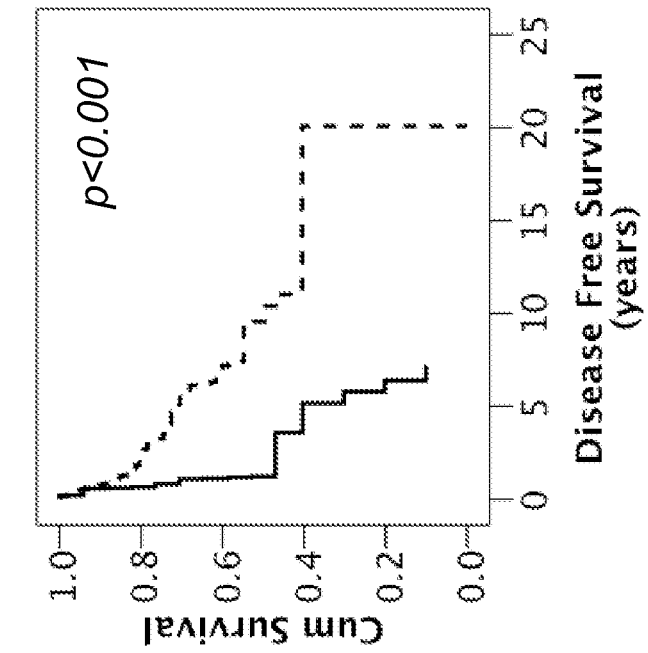
FIG. 3B shows DFS.
Figure 3A:
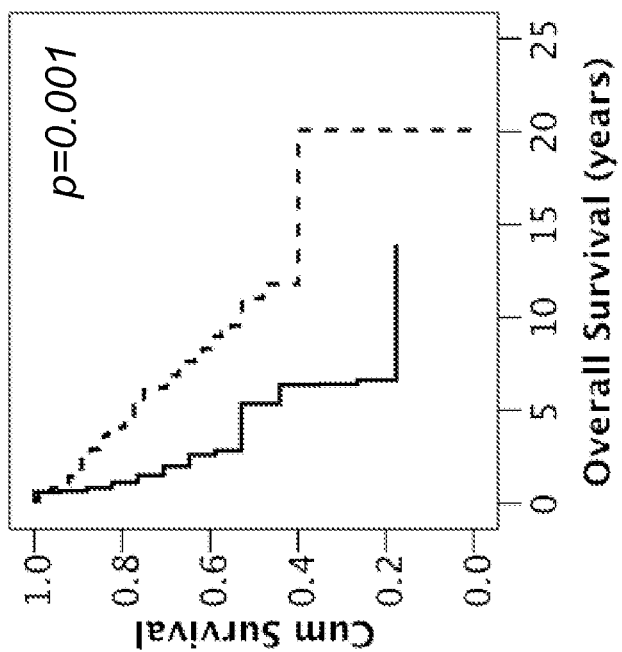
FIG. 3A shows OS.
Figures 4A, 4B:
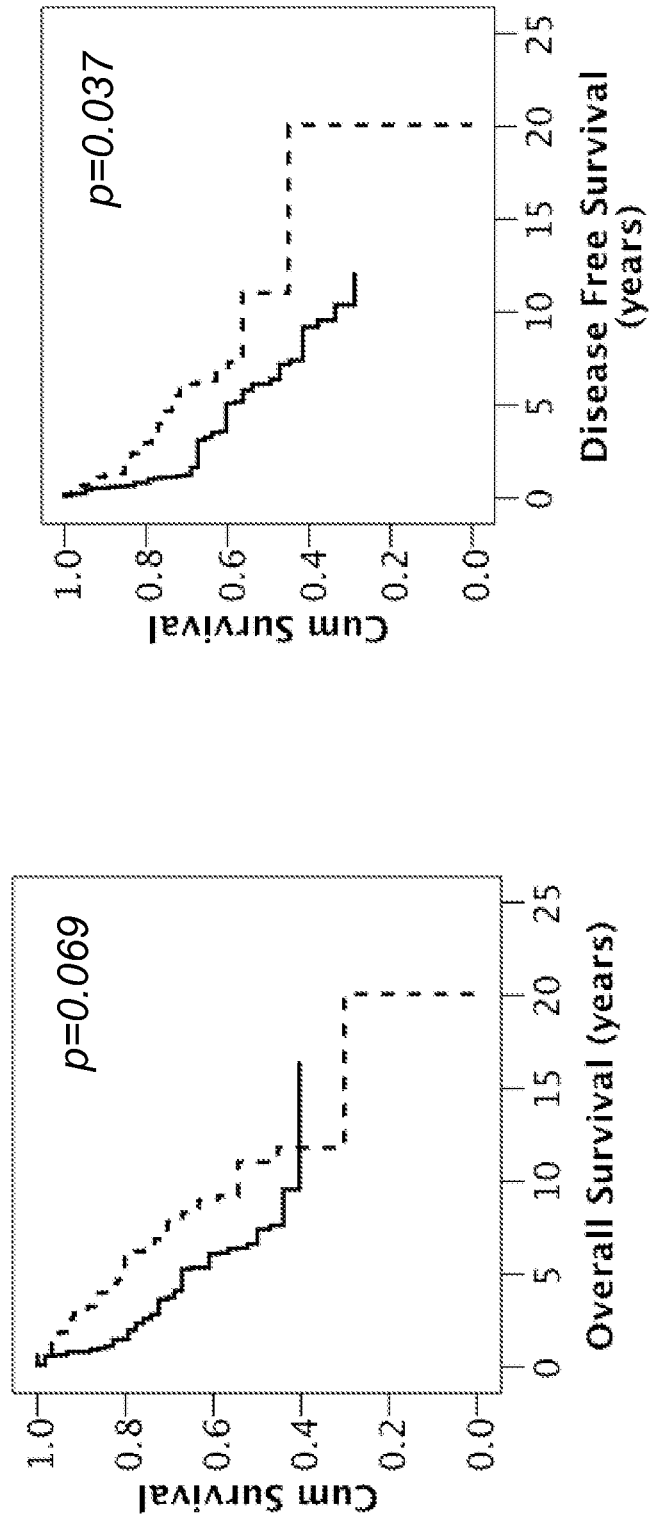
FIG. 4A shows OS.
FIG. 4B shows DFS.

Survival analysis of the entire cohort revealed that the nuclear fraction and nuclear intensity of stained tumor cells positive for anti-RBM3 significantly correlated with OS and DFS (FIG. 3-5), i.e. a high RBM3 protein level corresponded to a longer survival than a low RBM3 protein level. For example, patients having a fraction value of NF>0, five-year OS was approximately 79% (FIG. 3A). Patients having a RBM3 fraction value of NF=0 had an OS of about 52% (FIG. 3A), thus a surprisingly low OS given the OS of the whole group of patients as seen in FIG. 1A. It is seen in FIGS. 3-5 that both NI and NF levels are prognostically relevant. Further, it is seen that different cut-off:s may be employed for dividing a group of malignant melanoma subjects into two subgroups of different prognoses (FIGS. 3 and 4).

Further, the RBM3 protein level was also significantly correlated with OS and DFS in the subgroups of patients having SSM and/or NMM tumors (FIGS. 6-8). Consequently, patients diagnosed with SSM or NMM may be particularly suitable for analysis of RBM3 protein level. The prognostic indication appears to be more accentuated in NMM than in SSM (FIGS. 7 and 8).

Figure 9B:
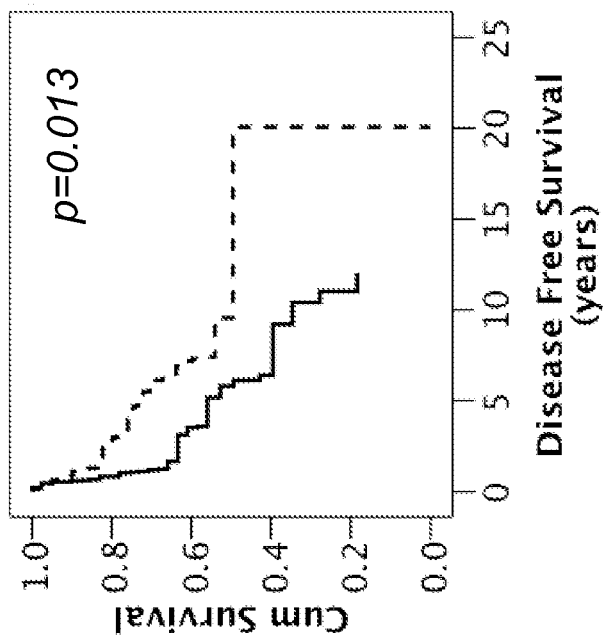
FIG. 9B shows DFS.
Figure 9A:
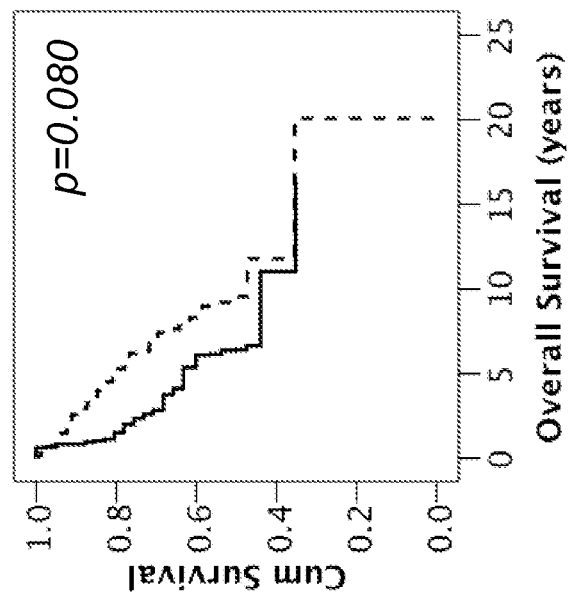
FIG. 9A shows OS.
Figure 10B:
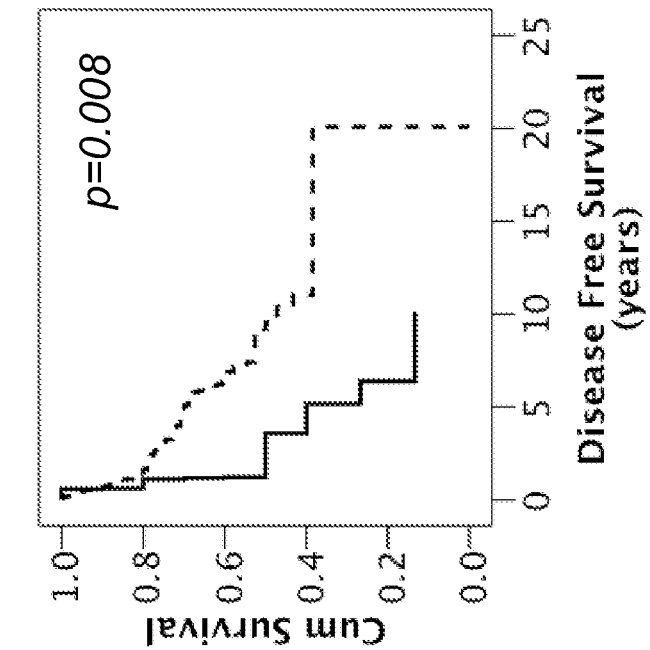
FIG. 10B shows DFS.
Figure 10A:
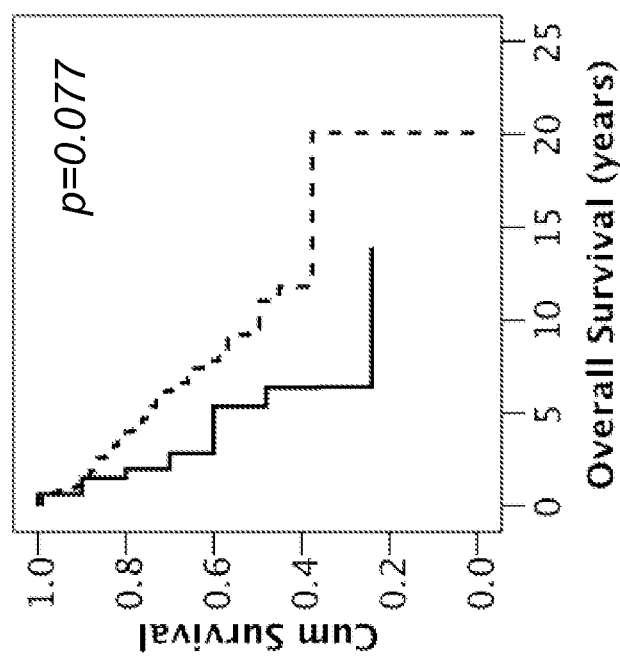
FIG. 10A shows OS.

Staining with 1B5 revealed similar results as obtained with anti-RBM3, the nuclear fraction—and nuclear intensity correlated well with OS (FIGS. 9A and 10A) and DFS (FIGS. 9B and 10B), i.e. a high RBM3 protein level corresponded to a longer survival than a low RBM3 protein level. FIGS. 9 and 10 further show that both NF and NI may be employed.

A correlation between RBM3 expression and number of metastases was observed. As seen in FIGS. 10A and 10B, low RBM3 expression in the primary tumor correspond to a probability of having metastasis of approximately 60-70%, whereas the probability is approximately 30% in case of RBM3 high primary tumors. Consequently, low RBM3 protein expression indicates a metastasizing cancer.

Epitope Mapping

5. Epitope Mapping Using Bacterial Display I

RBM3 DNA corresponding to SEQ ID NO:1 (i.e. aa 18-151 of ENSP00000365946 or by 261-682 ENST00000376755) was amplified by PCR using vector pAff8c as template. The amplified DNA was fragmentized to various lengths (approximately 50-150 bp) by sonication, followed by ligation into the staphylococcal display vector (pSCEM2) and transformed into S. Carnosus yielding around 100000 transformants. In-frame DNA fragments were displayed as peptides on the staphylococcal surface. After incubation with antibody (selective for SEQ ID NO:1, obtained as in Section 2 above) and fluorescently labeled secondary reagents, positive and negative cells were separately sorted using flow cytometry in order to isolate epitope and non-epitope presenting cells. Isolated cells were sequenced by pyrosequencing and sequences finally aligned to the RBM3 antigen for identification of epitopes.

A dual-labeling strategy with real-time monitoring of the surface expression level was used (Löfblom, J et al (2005) FEMS Microbiol Lett 248, 189-198). It allowed for normalization of the binding signal with the expression level, provided low cell-to-cell variations and made discrimination of different epitope populations possible. Further, it also allowed for a parallel assay to determine non-binding peptides displayed on the surface.
Two epitopes regions, SEQ ID NO:4 (RGFGFITFTNPE-HASVAMRAMNGESLDGR) and SEQ ID NO:5 (RSYS-RGGGDQGYGSGRYYDSRPGG), within SEQ ID NO:1 were identified.

6. Epitope Mapping Using Luminex a) Synthetic Peptide Preparation

A PEPscreen library consisting of 25 biotinylated peptides corresponding to the PrEST HPRR232631 (SEQ ID NO:1) on RBM3 was synthesized by Sigma-Genosys (Sigma-Aldrich). The peptides were 15 amino acids long with a 10 amino acid overlap, together covering the entire PrEST-sequence. The peptides were resolved in 80% DMSO to a final concentration of 10 mg/ml.

b) Bead Coupling

Neutravidin (Pierce, Rockford, Ill.) was immobilized on carboxylated beads (COOH Microspheres, Luminex-Corp., Austin, Tex.) in accordance to the manufacturer's protocol. Coupling of $10^6$ beads was performed using a filter membrane bottomed microtiter plate (MultiScreen-HTS, Millipore, Billerica, Mass.) as previously described (Larsson et al (2009) J Immunol Methods 15; 34(1-2):20-32, Schwenk et al (2007) Mol Cell Proteomics 6(1) 125:32). 25 distinct groups of beads with different color code IDs were activated using 1-Ethyl-3-(3-dimethylamino-propyl) carbodiimide and N-Hydroxysuccinimide. Neutravidin (100 µg/ml in MES) was added to the beads and incubated for 120 min on a shaker. The beads were finally washed, re-suspended, and transferred to microcentrifuge tubes for storage at 4° C. in a protein containing buffer (BRE, Blocking Reagent for ELISA, Roche, Basel, Switzerland) supplemented with NaN3. All coupled bead populations were treated with sonication in an ultrasonic cleaner (Branson Ultrasonic Corporation, Danbury, Conn.) for 5 min. The biotinylated peptides were diluted in BRE to a concentration of 20 µM, and 100 µl of each peptide was used in the coupling reaction, which was conducted for 60 min with shaking at RT. Finally, the beads were washed with 3×100 µl BRE buffer and stored at 4° C. until further use.

c) Determination of Binding Specificity

A bead mixture containing all 25 bead IDs was prepared and 45 µl of each antibody diluted to 50 ng/ml in PBS was mixed with 5 µl of the bead mix and incubated for 60 min at RT. A filter bottomed microtiter plate (Millipore) was utilized for washing and following each incubation all wells were washed with 3×100 µl PBST. 50 µl of R-Phycoerythrine labeled anti-rabbit IgG antibody (0.5 µg/ml, Jackson ImmunoResearch) or 50 µl of Alexa Fluor 555 goat anti-mouse IgG were added (0.4 ug/ml) for a final incubation of 60 min at RT.

Measurements were performed using the Luminex LX200 instrumentation with Luminex xPONENT software. For each experiment 50 events per bead ID were counted and the median fluorescence intensity (MFI) was used as a measurement of antibody binding to individual bead populations.

d) Results

The specificities of the monospecific polyclonal antibody (anti-RBM3, HPA003624) and the monoclonal antibody 6F11 were tested in an assay using beads coupled with synthetic biotinylated peptides. Anti-RBM3 showed strong binding to 8 of the peptides, namely 6, 7, 8, 14, 15, 16, 24 and 25, corresponding to three distinct regions on the PrEST sequence, consensus sequences SEQ ID NO: 6, 7, 8 and 9. In particular peptide 24 and 25, corresponding to SEQ ID NO:9 generated a strong signal. The monoclonal antibody 6F11 reacted with two peptides: 15 and 16, corresponding to one distinct region on the PrEST sequence, consensus sequence SEQ ID NO: 8. As both anti-RBM3 and 6F11 bound to peptides 15 and 16, this indicates that these antibodies share one or more epitope(s) within this region. It is notable that SEQ ID NO:6 is within SEQ ID NO:4 and that SEQ ID NO:8 to some extent overlaps with SEQ ID NO:5.

7. Epitope Mapping Using Bacterial Display II

RBM3 DNA corresponding to SEQ ID NO:1 (i.e. aa 18-151 of ENSP00000365946 or by 261-682 ENST00000376755) was amplified by PCR using vector pAff8c as template. The amplified DNA was fragmentized to various lengths (approximately 50-150 bp) by sonication, followed by ligation into the staphylococcal display vector (pSCEM2) and transformed into S. Carnosus yielding around 100000 transformants. In-frame DNA fragments were displayed as peptides on the staphylococcal surface. After incubation with antibody (anti-RBM3 obtained in Section 2 and monoclonal antibodies obtained in Section 3) and fluorescently labeled secondary reagents, positive and negative cells were separately sorted using flow cytometry in order to isolate epitope and non-epitope presenting cells. Plasmid DNA from isolated cells was sequenced by Sanger sequencing and sequences were aligned to the RBM3 antigen for identification of epitopes.

A dual-labeling strategy with real-time monitoring of the surface expression level was used (Löfblom, J et al (2005) FEMS Microbiol Lett 248, 189-198). It allowed for normalization of the binding signal with the expression level, provided low cell-to-cell variations and made discrimination of different epitope populations possible. Further, it also allowed for a parallel assay to determine non-binding peptides displayed on the surface.

For the polyclonal antibody, the regions SEQ ID NO:10-15 within SEQ ID NO:1, were identified. In particular, the regions SEQ ID NO:11 and SEQ ID NO:12 were of interest, since they were found within the earlier identified region SEQ ID NO:4. Further, the regions SEQ ID NO:13 and 14 were particularly interesting, since they to a large extent overlapped with previously identified SEQ ID NO:6 and 7, respectively.

For the monoclonal antibody 6F11, the region SEQ ID NO:16 within SEQ ID NO:1 was identified, and this region (SEQ ID NO:16) is within the earlier identified region SEQ ID NO:5. The epitope region of 6F11 identified here in Section 7 has a one-amino acid overlap with the 6F11 epitope region identified in Section 6. The results of Sections 6 and 7 are, however, not in contrast; one of the peptides found to bind 6F11 in Section 6 (peptide 16) comprises SEQ ID NO:16 (and SEQ ID NO:19). The results of Sections 6 and 7 may thus be considered complementary.

For the monoclonal antibody 1B5, the region SEQ ID NO:17 within SEQ ID NO:1 was identified, and this region (SEQ ID NO:17) was also found within the earlier identified region SEQ ID NO:5. For the monoclonal antibody 7G3, the region SEQ ID NO:18 within SEQ ID NO:1 was identified. This region (SEQ ID NO:18) was also found within the earlier identified region SEQ ID NO:5. This region (SEQ ID NO:18) overlaps with the epitope for the 6F11 antibody (SEQ ID NO:16). For the monoclonal antibody 9B11, the region SEQ ID NO:19 within SEQ ID NO:1 was identified.

8. Evaluation of Antibody Specificity a) Material and Methods

The specificity of the polyclonal antibody (anti-RBM3), and two of the monoclonal antibodies (6F11 and 1B5) were analysed by Western Blot. Western blot was performed by separation of total protein extracts from selected human cell lines on 17% SDS-PAGE gels under reducing conditions, followed by electro-transfer to PVDF membranes (Bio-Rad Laboratories) according to the manufacturer's recommendations. The membranes were blocked (5% BSA in 1×PBS with 0.1% Tween20) for 1 h at room temperature, incubated with the primary affinity purified antibody (diluted 1:1000 in blocking buffer) and washed in PBST. The secondary HRP-conjugated antibody (sheep anti-mouse immunoglobulin/HRP, GE) was diluted 1:10000 in blocking buffer and chemiluminescence detection was carried out using a Chemidoc™ CCD camera (Bio-Rad Laboratories) and Western Blotting Luminol Reagent (Santa Cruz Biotechnologies, Inc), according to the manufacturer's protocol.

b) Results

The results of the Western blot analysis shows that the antibodies specifically detect a band of approximately 16 kDa in the cell lines. The theoretical molecular weight of RBM3 is 16 kDa (as calculated from the RBM3 amino acid sequence SEQ ID NO:2), corresponding well to the result obtained. Additional bands were observed for anti-RBM3 and 6F11. Overall, the results show that the monoclonal antibodies were more specific than the polyclonal antibody, and that the 1B5 antibody was even more specific than the 6F11 antibody (see FIG. 12).

Establishment of a prognosis

9. A Non-Limiting Example

Following the establishment of a malignant melanoma in a patient, a tumor tissue sample from the patient is obtained. The tumor tissue sample may be obtained from a specimen from an earlier surgical removal of the tumor. Further, for the provision of a "negative reference", a sample is taken from archival material comprising tissue having low, or essentially lacking, RBM3 protein expression. Such archival tissue may for example be malignant melanoma tissue having a pre-established low RBM3 protein expression level. Further, for the provision of a "positive reference", a sample is taken from archival material comprising tissue having high RBM3 protein expression, such as malignant melanoma tissue having a pre-established high RBM3 protein expression level.

The sample material is fixated in buffered formalin and histo-processed in order to obtain thin sections (4 μm) of the sample material.

Immunohistochemistry is performed in line with what is described in Examples, Section 4. One or more sample sections from each sample is/are mounted on glass slides that are incubated for 45 min in 60° C., de-paraffinized (if the sample in question was paraffinized) in xylene (2×15 min) and hydrated in graded alcohols. For antigen retrieval, slides are immersed in TRS (Target Retrieval Solution, pH 6.0, DakoCytomation) and boiled for 4 min at 125° C. in a Decloaking Chamber® (Biocare Medical). Slides are placed in the Autostainer® (DakoCytomation) and endogenous peroxidase is initially blocked with $H_2O_2$ (DakoCytomation). The reason for mounting multiple sample sections is to increase the accuracy of the results.

A primary RBM3 protein specific antibody (e.g. a monospecific polyclonal anti-RBM3 antibody obtained as in Examples, Section 2) is added to the slides and incubated for 30 min in room temperature, followed by 30 min of incubation in room temperature with a labeled secondary antibody; e.g. goat-anti-rabbit peroxidase conjugated Envision®. To detect the secondary antibody, diaminobenzidine (DakoCytomation) is used as chromogen, contrasted with a Harris hematoxylin (Sigma-Aldrich) counterstaining. Between all steps, slides are rinsed in wash buffer (DakoCytomation). The slides are then mounted with Pertex® (Histolab) mounting media.

Optionally, two control cell-lines may be used as a tool to validate the staining procedure; e.g. one slide with cells expressing RBM3 protein (positive cell line) and one slide having cells with indistinct weak or no RBM3 protein expression (negative cell line). The skilled artisan understands how to provide such cell lines, for example guided by the disclosure of Rhodes et al. (2006) The biomedical scientist, p 515-520. The control-line slides may be simultaneously stained in the same procedure as the other slides, i.e. incubated with the same primary and secondary antibodies.

For example, the tumor tissue slides from the subject, the staining reference slides, and optionally, the slides with control cell-lines, may be scanned in a light microscope using a ScanScope T2 automated slide scanning system (Aperio Technologies) at ×20 magnification. However, this scanning step is not necessary, but may make the procedure easier if, for example, the preparation and staining of the slides and the evaluation of the stained slides (see below) are performed at different locations or by different persons.

If control cell-lines are used, these are inspected to validate the staining procedure. If the cell-lines display staining results outside acceptable criteria, e.g. staining artifacts recognized by the skilled artisan, the staining of the tissue samples is considered invalid and the whole staining procedure is repeated with new slides. If the positive and negative cell-lines display strong staining intensity and indistinct weak or no staining intensity, respectively, the staining is considered as valid.

The stained sample slide(s) from the tumor tissue is/are evaluated manually by visual inspection in accordance to standards used in clinical histo-pathological diagnostics, and the immunoreactivity of the colorectal cancer slide(s) is/are graded in accordance with Examples, Section 4 above.

That is, the nuclear intensity (NI) and the nuclear fraction (NF) are examined. The person performing the evaluation and determination is aided by visual inspection of the stained positive and negative reference slides.

The sample value(s) from the tumor tissue sample from the patient is/are then compared to a reference value. If more than one sample slide are evaluated and thereby more than one sample value are obtained, the sample value that is compared to the reference value may be a mean or median value of the obtained sample values.

Figure 5B:
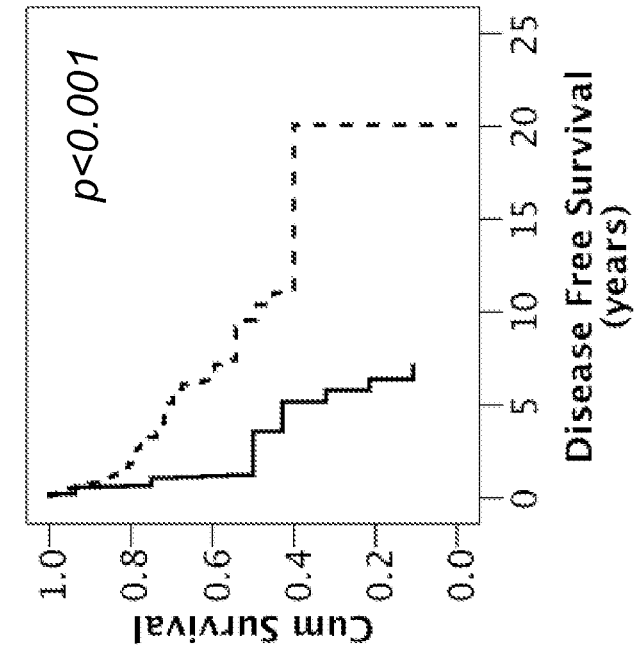
FIG. 5B shows DFS.
Figure 5A:
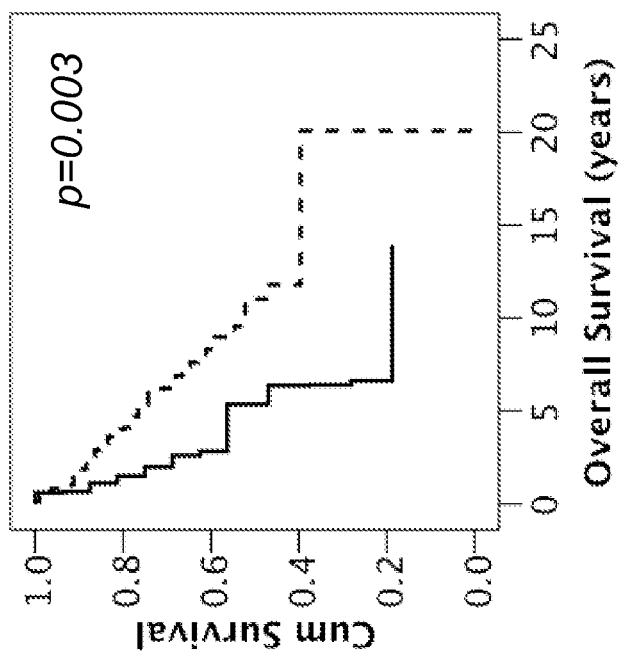
FIG. 5A shows OS.

The reference value may be an absent NI. In such case it is concluded that the tested patient belongs to a group of patients having a relatively good prognosis if the sample value is a weak, moderate or strong NI and a group of patients having a relatively poor prognosis if the sample the sample value is an absent NI. The prognoses of the respective groups may be read from dichotomized data as those presented in FIG. 5, wherein the upper curve represents the group of patients having the relatively good prognosis and the lower curve represents the group of patients having the relatively poor prognosis. For example, the relatively good prognosis may be an average five-year overall survival of about 76% and the relatively poor prognosis may be an average five-year overall survival of about 56% (FIG. 5A). Alternatively, the relatively good prognosis may be an average five-year disease free survival of about 72% and the poor prognosis may be an average five-year disease free survival of about 42% (FIG. 5B).

Figure 8B:
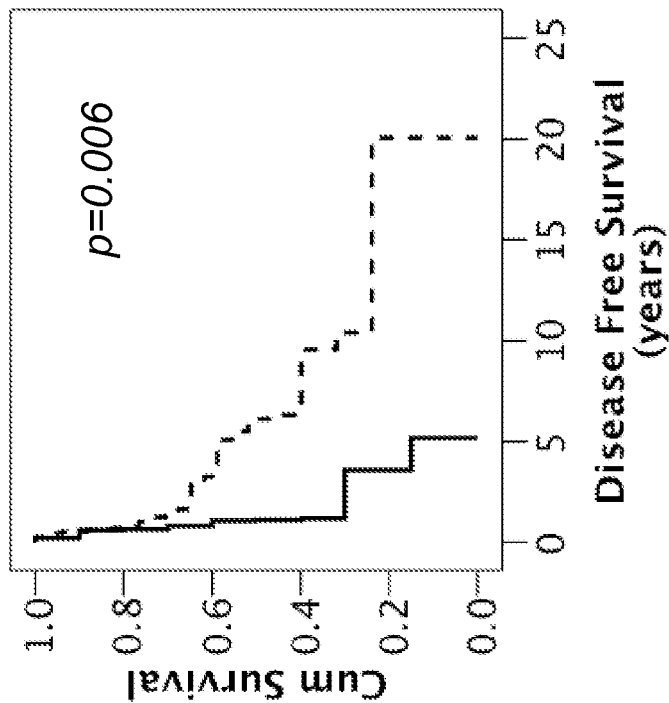
FIG. 8B shows DFS.
Figure 8A:
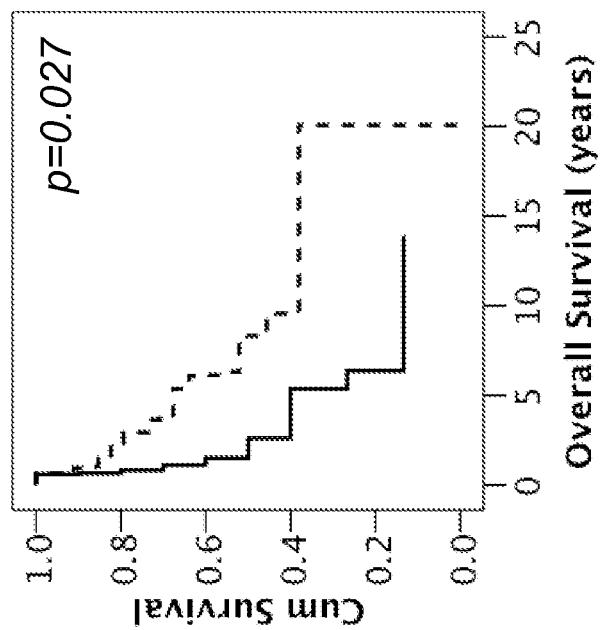
FIG. 8A shows OS.

Further, the reference value may be a NF of 0-1%. In such case it is concluded that the tested patient belongs to a group of patients having a relatively good prognosis if the NF of the sample is 2-100% and a group of patients having a relatively poor prognosis if the NF of the sample is 0-1%. If the patient in question has NMM, the prognoses of the respective groups may be read from dichotomized data as those presented in FIG. 8, which are based on patients having NMM, exclusively. In FIG. 8, the upper curve represents the group of patients having the relatively good prognosis and the lower curve represents the group of patients having the relatively poor prognosis. For example, the relatively good prognosis may be an average five-year overall survival of about 68% and the relatively poor prognosis may be an average five-year overall survival of about 40% (FIG. 8A). Alternatively, the relatively good prognosis may be an average five-year disease free survival of about 55% and the poor prognosis may be an average five-year disease free survival of about 15% (FIG. 8B).

All cited material, including but not limited to publications, DNA or protein data entries, and patents, referred to in this application are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method of examining a subject having a malignant melanoma, comprising:
   a) immunohistochemically evaluating an amount of RBM3 protein present in at least part of a malignant melanoma tissue sample from the subject and determining a sample value corresponding to the evaluated amount;
   b) comparing the sample value obtained in step a) with a reference value; and,
   if said sample value is equal to or lower than said reference value,
   c) performing a node biopsy on at least one lymph node, wherein the biopsy may be used for establishing whether the malignant melanoma of said subject has spread to the respective lymph node.

2. The method according to claim 1, wherein said malignant melanoma is a superficial spreading melanoma (SSM) or a nodular malignant melanoma (NMM).

3. The method according to claim 1, wherein said sample comprises tumor cells from said subject.

4. The method according to claim 3, wherein the evaluation of step a) is limited to the nuclei of tumor cells of said sample.

5. The method according to claim 1, wherein the reference value of step b) corresponds to a reference sample having no detectable RBM3 protein.

6. The method according to claim 1, wherein step a) comprises:
   aI) applying to said sample a quantifiable antibody, fragment thereof, or derivative thereof capable of selective interaction with the RBM3 protein to be evaluated, said application being performed under conditions that enable binding of the antibody, fragment thereof, or derivative thereof to RBM3 protein present in the sample; and
   aII) quantifying the antibody, fragment thereof, or derivative thereof bound to said sample to evaluate said amount.

7. The method according to claim 6, wherein said quantifiable antibody, fragment thereof, or derivative thereof is capable of selective interaction with a peptide whose amino acid sequence consists of a sequence SEQ ID NO:1.

8. The method according to claim 6, wherein said quantifiable antibody, fragment thereof, or derivative thereof is capable of selective interaction with a peptide consisting of an amino acid sequence selected from SEQ ID NO:4 and 5.

9. The method according to claim 6, wherein said quantifiable antibody, fragment thereof, or derivative thereof is capable of selective interaction with a RBM3 fragment which consists of 20 amino acids or less and comprises an amino acid sequence selected from SEQ ID NO:6-19.

10. The method according to claim 6, wherein said quantifiable antibody, fragment thereof, or derivative thereof is capable of selective interaction with:
- a peptide whose amino acid sequence consists of SEQ ID NO:5; or
- a RBM3 fragment which consists of 20 amino acids or less and comprises an amino acid sequence selected from SEQ ID NO:8, 16 and 17.

* * * * *

SEQUENCE LISTING

<160> NUMBER OF SEQ ID NOS: 21

<210> SEQ ID NO 1
<211> LENGTH: 134
<212> TYPE: PRT
<213> ORGANISM: Homo sapiens

<400> SEQUENCE: 1

Asp Glu Gln Ala Leu Glu Asp His Phe Ser Ser Phe Gly Pro Ile Ser
1               5                   10                  15

Glu Val Val Val Lys Asp Arg Glu Thr Gln Arg Ser Arg Gly Phe
            20                  25                  30

Gly Phe Ile Thr Phe Thr Asn Pro Glu His Ala Ser Val Ala Met Arg
        35                  40                  45

Ala Met Asn Gly Glu Ser Leu Asp Gly Arg Gln Ile Arg Val Asp His
    50                  55                  60

Ala Gly Lys Ser Ala Arg Gly Thr Arg Gly Gly Gly Phe Gly Ala His
65                  70                  75                  80

Gly Arg Gly Arg Ser Tyr Ser Arg Gly Gly Gly Asp Gln Gly Tyr Gly
                85                  90                  95

Ser Gly Arg Tyr Tyr Asp Ser Arg Pro Gly Gly Tyr Gly Tyr Gly Tyr
            100                 105                 110

Gly Arg Ser Arg Asp Tyr Asn Gly Arg Asn Gln Gly Gly Tyr Asp Arg
        115                 120                 125

Tyr Ser Gly Gly Asn Tyr
    130

<210> SEQ ID NO 2

<211> LENGTH: 157
<212> TYPE: PRT
<213> ORGANISM: Homo sapiens

<400> SEQUENCE: 2

```
Met Ser Ser Glu Glu Gly Lys Leu Phe Val Gly Gly Leu Asn Phe Asn
1               5                   10                  15

Thr Asp Glu Gln Ala Leu Glu Asp His Phe Ser Ser Phe Gly Pro Ile
            20                  25                  30

Ser Glu Val Val Val Lys Asp Arg Glu Thr Gln Arg Ser Arg Gly
        35                  40                  45

Phe Gly Phe Ile Thr Phe Thr Asn Pro Glu His Ala Ser Val Ala Met
50                  55                  60

Arg Ala Met Asn Gly Glu Ser Leu Asp Gly Arg Gln Ile Arg Val Asp
65                  70                  75                  80

His Ala Gly Lys Ser Ala Arg Gly Thr Arg Gly Gly Phe Gly Ala
            85                  90                  95

His Gly Arg Gly Arg Ser Tyr Ser Arg Gly Gly Gly Asp Gln Gly Tyr
            100                 105                 110

Gly Ser Gly Arg Tyr Tyr Asp Ser Arg Pro Gly Gly Tyr Gly Tyr Gly
            115                 120                 125

Tyr Gly Arg Ser Arg Asp Tyr Asn Gly Arg Asn Gln Gly Gly Tyr Asp
            130                 135                 140

Arg Tyr Ser Gly Gly Asn Tyr Arg Asp Asn Tyr Asp Asn
145                 150                 155
```

<210> SEQ ID NO 3
<211> LENGTH: 1130
<212> TYPE: DNA
<213> ORGANISM: Homo sapiens

<400> SEQUENCE: 3

| | | |
|---|---|---|
| atgcgcaatg tggccccta atggtggctg cgctgagcca gctcctcaga ttaccacctt | 60 |
| attggccgcc tttctcagct tttctgtagt tacccatatt ttgttcctct ttcttgtcta | 120 |
| ttttctgtgc ttttctctg ctttccgtct cgctattttc tcacatctcc attttctttc | 180 |
| tccttcctgc caccattctt catgttcttc ccacaggact tgaactgcca tgtcctctga | 240 |
| agaaggaaag ctcttcgtgg gagggctcaa ctttaacacc gacagcagg cactggaaga | 300 |
| ccacttcagc agtttcggac ctatctctga ggtggtcgtt gtcaaggacc gggagactca | 360 |
| gcggtccagg ggttttggtt tcatcacctt caccaaccca gagcatgctt cagttgccat | 420 |
| gagagccatg aacggagagt ctctggatgg tcgtcagatc cgtgtggatc atgcaggcaa | 480 |
| gtctgctcgg ggaaccagag aggtggctt tggggcccat gggcgtggtc gcagctactc | 540 |
| tagaggtggt ggggaccagg gctatgggag tggcaggtat tatgacagtc gacctggagg | 600 |
| gtatggatat ggatatggac gttccagaga ctataatggc agaaaccagg gtggttatga | 660 |
| ccgctactca ggaggaaatt acagagacaa ttatgacaac tgaaatgaga catgcacata | 720 |
| atatagatac acaaggaata atttctgatc caggatcgtc cttccaaatg gctgtattta | 780 |
| taaaggtttt tggagctgca ccgaagcatc ttatttata gtatatcaac cttttgtttt | 840 |
| taaattgacc tgccaaggta gctgaagacc tttagacag ttccatcttt ttttttaaat | 900 |
| tttttctgcc tatttaaaga caaattatgg gacgtttgta gaacctgagt attttctttt | 960 |
| ttaccagttt tttagtttga gctcttaggt ttattggagc tagcaataat tggttctggc | 1020 |
| aagtttggcc agactgactt caaaaaatta atgtgtatcc agggacattt taaaaacctg | 1080 |

```
tacacagtgt ttattgtggt taggaagcaa tttcccaatg tacctataag            1130
```

<210> SEQ ID NO 4
<211> LENGTH: 29
<212> TYPE: PRT
<213> ORGANISM: Homo sapiens

<400> SEQUENCE: 4

Arg Gly Phe Gly Phe Ile Thr Phe Thr Asn Pro Glu His Ala Ser Val
1               5                   10                  15

Ala Met Arg Ala Met Asn Gly Glu Ser Leu Asp Gly Arg
            20                  25

<210> SEQ ID NO 5
<211> LENGTH: 24
<212> TYPE: PRT
<213> ORGANISM: Homo sapiens

<400> SEQUENCE: 5

Arg Ser Tyr Ser Arg Gly Gly Gly Asp Gln Gly Tyr Gly Ser Gly Arg
1               5                   10                  15

Tyr Tyr Asp Ser Arg Pro Gly Gly
            20

<210> SEQ ID NO 6
<211> LENGTH: 5
<212> TYPE: PRT
<213> ORGANISM: Homo sapiens

<400> SEQUENCE: 6

Thr Phe Thr Asn Pro
1               5

<210> SEQ ID NO 7
<211> LENGTH: 10
<212> TYPE: PRT
<213> ORGANISM: Homo sapiens

<400> SEQUENCE: 7

Gly Thr Arg Gly Gly Gly Phe Gly Ala His
1               5                   10

<210> SEQ ID NO 8
<211> LENGTH: 10
<212> TYPE: PRT
<213> ORGANISM: Homo sapiens

<400> SEQUENCE: 8

Gly Phe Gly Ala His Gly Arg Gly Arg Ser
1               5                   10

<210> SEQ ID NO 9
<211> LENGTH: 5
<212> TYPE: PRT
<213> ORGANISM: Homo sapiens

```
<400> SEQUENCE: 9

Tyr Asp Arg Tyr Ser
1               5

<210> SEQ ID NO 10
<211> LENGTH: 9
<212> TYPE: PRT
<213> ORGANISM: Homo sapiens

<400> SEQUENCE: 10

Asp Glu Gln Ala Leu Glu Asp His Phe
1               5

<210> SEQ ID NO 11
<211> LENGTH: 7
<212> TYPE: PRT
<213> ORGANISM: Homo sapiens

<400> SEQUENCE: 11

Thr Asn Pro Glu His Ala Ser
1               5

<210> SEQ ID NO 12
<211> LENGTH: 10
<212> TYPE: PRT
<213> ORGANISM: Homo sapiens

<400> SEQUENCE: 12

Glu His Ala Ser Val Ala Met Arg Ala Met
1               5                   10

<210> SEQ ID NO 13
<211> LENGTH: 10
<212> TYPE: PRT
<213> ORGANISM: Homo sapiens

<400> SEQUENCE: 13

Arg Gly Gly Gly Phe Gly Ala His Gly Arg
1               5                   10

<210> SEQ ID NO 14
<211> LENGTH: 8
<212> TYPE: PRT
<213> ORGANISM: Homo sapiens

<400> SEQUENCE: 14

Gly Phe Gly Ala His Gly Arg Gly
1               5

<210> SEQ ID NO 15
<211> LENGTH: 9
<212> TYPE: PRT
<213> ORGANISM: Homo sapiens

<400> SEQUENCE: 15

Asp Tyr Asn Gly Arg Asn Gln Gly Gly
1               5

<210> SEQ ID NO 16
<211> LENGTH: 5
<212> TYPE: PRT
<213> ORGANISM: Homo sapiens

<400> SEQUENCE: 16

Ser Tyr Ser Arg Gly
```

-continued

```
<210> SEQ ID NO 17
<211> LENGTH: 11
<212> TYPE: PRT
<213> ORGANISM: Homo sapiens

<400> SEQUENCE: 17

Asp Gln Gly Tyr Gly Ser Gly Arg Tyr Tyr Asp
1               5                   10

<210> SEQ ID NO 18
<211> LENGTH: 6
<212> TYPE: PRT
<213> ORGANISM: Homo sapiens

<400> SEQUENCE: 18

Ser Tyr Ser Arg Gly Gly
1               5

<210> SEQ ID NO 19
<211> LENGTH: 3
<212> TYPE: PRT
<213> ORGANISM: Homo sapiens

<400> SEQUENCE: 19

Asp Glu Gln
1

<210> SEQ ID NO 20
<211> LENGTH: 19
<212> TYPE: DNA
<213> ORGANISM: Homo sapiens

<400> SEQUENCE: 20
gacgagcagg cactggaag                                                    19

<210> SEQ ID NO 21
<211> LENGTH: 20
<212> TYPE: DNA
<213> ORGANISM: Homo sapiens

<400> SEQUENCE: 21
gtaatttcct cctgagtagc                                                   20
```